US010208129B2

(12) United States Patent
Tikhomirov et al.

(10) Patent No.: US 10,208,129 B2
(45) Date of Patent: Feb. 19, 2019

(54) ANTIBODIES SELECTIVE FOR CELLS PRESENTING ERBB2 AT HIGH DENSITY

(75) Inventors: Ilia Alexandre Tikhomirov, Toronto (CA); Maria L. Jaramillo, Beaconsfield (CA); Maureen D. O'Connor-McCourt, Beaconsfield (CA); Traian Sulea, Kirkland (CA); Renald Gilbert, Montreal (CA); Bruno Gaillet, Sainte Julienne (CA); Jason Baardsnes, Montreal (CA)

(73) Assignee: National Research Council of Canada, Ottawa (CA)

( * ) Notice: Subject to any disclaimer, the term of this patent is extended or adjusted under 35 U.S.C. 154(b) by 464 days.

(21) Appl. No.: 13/992,051

(22) PCT Filed: Dec. 2, 2011

(86) PCT No.: PCT/CA2011/050747
§ 371 (c)(1),
(2), (4) Date: Jun. 19, 2013

(87) PCT Pub. No.: WO2012/075581
PCT Pub. Date: Jun. 14, 2012

(65) Prior Publication Data
US 2013/0266564 A1  Oct. 10, 2013

Related U.S. Application Data

(60) Provisional application No. 61/419,983, filed on Dec. 6, 2010.

(51) Int. Cl.
*C07K 16/32* (2006.01)
(52) U.S. Cl.
CPC .......... *C07K 16/32* (2013.01); *C07K 2317/24* (2013.01); *C07K 2317/565* (2013.01); *C07K 2317/92* (2013.01)
(58) Field of Classification Search
CPC ................................ C07K 16/18; C07K 16/28
See application file for complete search history.

(56) References Cited

U.S. PATENT DOCUMENTS

| | | |
|---|---|---|
| 3,773,919 A | 11/1973 | Boswell |
| 5,869,046 A | 2/1999 | Presta et al. |
| 6,121,022 A | 9/2000 | Presta et al. |
| 6,194,551 B1 | 2/2001 | Idusogie et al. |
| 7,435,797 B2 | 10/2008 | Lowman et al. |
| 2003/0153043 A1 | 8/2003 | Carr et al. |
| 2011/0177095 A1* | 7/2011 | Harding ............ C07K 16/32 424/172.1 |

FOREIGN PATENT DOCUMENTS

| | | | |
|---|---|---|---|
| EP | 0 616 812 | 9/1994 | |
| WO | WO1994/029351 | 12/1994 | |
| WO | WO 2005092925 A2 * | 10/2005 | ............. C07K 16/00 |
| WO | WO2012/075581 | 6/2012 | |

OTHER PUBLICATIONS

Bostrom, J. et al., Science, 323: 1610-1614, Mar. 20, 2009.*
Carter, P., et al., Proc. Natl. Acad. Sci. USA, 89: 4285-4289, 1992.*
Almagro and Fransson, Frontiers in Bioscience, 13: 1619-1633, 2008.*
Hanf, K.J.M., et al. Methods 65: 68076, 2014.*
Cho et al., "Structure of the extracelllar region of HER2 alone and in complex with the Herceptin Fab," Nature. vol. 421, No. 6924 pp. 756-760 (2003).
GenBank CAA04739.1. Ottensmeier et al., "Analysis of VH genes in follicular and diffuse lymphoma shows ongoing somatic mutation and multiple isotype transcripts in early disease with changes during disease progression," Blood. vol. 91, N. 11 pp. 4292-4299 (1998).
Li, Z., and Scheraga, H.A., "Monte Carlo-minimization approach to the multiple-minima problem in protein folding," PNAS. vol. 84 pp. 6611-6615 (1987).
Moynagh, J., and Schimmel, H., "Tests for BSE evaluated," Nature. vol. 400 p. 105 (1999).
Mullick et al., "The cumate gene-switch: a system for regulated expression in mammalian cells," BMC Biotechnology. vol. 6 p. 43 (2006).
Notification of Transmittal of the International Search Report and the Written Opinion of the International Searching Authority, or the Declaration corresponding to International Patent Application No. PCT/CA2011/050747 dated Mar. 20, 2012.
Selzer, "Rational Design of Faster Associating and Tighter Binding Protein Complexes," Nat. Struct. Mol. Biol. vol. 7 pp. 537-541 (2000).
UniProtKB/Swiss-Prot: P04626.1. Yamamoto et al., "Similarity of protein encoded by the human c-erb-B-2 gene to epidermal growth factor receptor," Nature. vol. 319, No. 6050 pp. 230-234 (1986).

(Continued)

*Primary Examiner* — Brad Duffy
(74) *Attorney, Agent, or Firm* — Jenkins, Wilson, Taylor & Hunt, P.A.

(57) ABSTRACT

An erbB2 antibody is provided that binds preferentially to disease cells having an erbB2 density greater than a normal erbB2 density. The erbB2 antibody comprises a heavy chain and a light chain. Each chain has a constant region and a variable region. Each variable region comprises framework regions and complementarity determining regions (CDRs), wherein the CDRs have an amino acid sequence set forth below: For the heavy chain: CDR1 GFNIKDTYIH (SEQ ID No. 1) CDR2 RIYPTNGY$^{57}$TR$^{59}$ YADSVKG (SEQ ID No. 2) CDR3 WGGDGFYAMDY (SEQ ID No. 3) For the light chain: CDR1 RASQDVN$^{30}$TAVA (SEQ ID No. 4) CDR2 SASF$^{53}$LYS (SEQ ID No. 5) CDR3 QQHY$^{92}$TTPPT (SEQ ID No. 6). At least one of Y57, R59, N30, F53, and Y92 is substituted by an amino acid that confers on said antibody a reduced erbB2 binding affinity (Kd) that is in the range from 0.1 nM to 100 nM. The substitution is other than N30A, F53N, Y92A and Y92F when there is a single substitution in the antibody light chain.

12 Claims, 4 Drawing Sheets

Specification includes a Sequence Listing.

(56) References Cited

OTHER PUBLICATIONS

Gaillet et al., "High-Level Recombinant Protein Production in CHO Cells Using an Adenoviral Vector and the Cumate Gene-Switch," Biotechnol. Prog. vol. 23 pp. 200-209 (2007).

Gerstner et al., "Sequence plasticity in the antigen-binding site of a therapeutic anti-HER2 antibody," Journal of Molecular Biology. vol. 321, No. 5 pp. 851-862 (2002).

Kelley, R.F., and O'Connell, M.P., "Thermodynamic analysis of an antibody functional epitope," Biochemistry. vol. 32, No. 27 pp. 6828-6835 (1993).

Naïm et al., "Solvated Interaction Energy (SIE) for Scoring Protein-Ligand Binding Affinities. 1. Exploring the Parameter Space," Journal of Chemical Information and Modeling. vol. 47, No. 1 pp. 122-133 (2007).

Vivcharuk et al. (Jul. 27, 2017) Assisted Design of Antibody and Protein Therapeutics (ADAPT). PLOS ONE 12(7):e0181490:1-17.

* cited by examiner

Figure 2C:
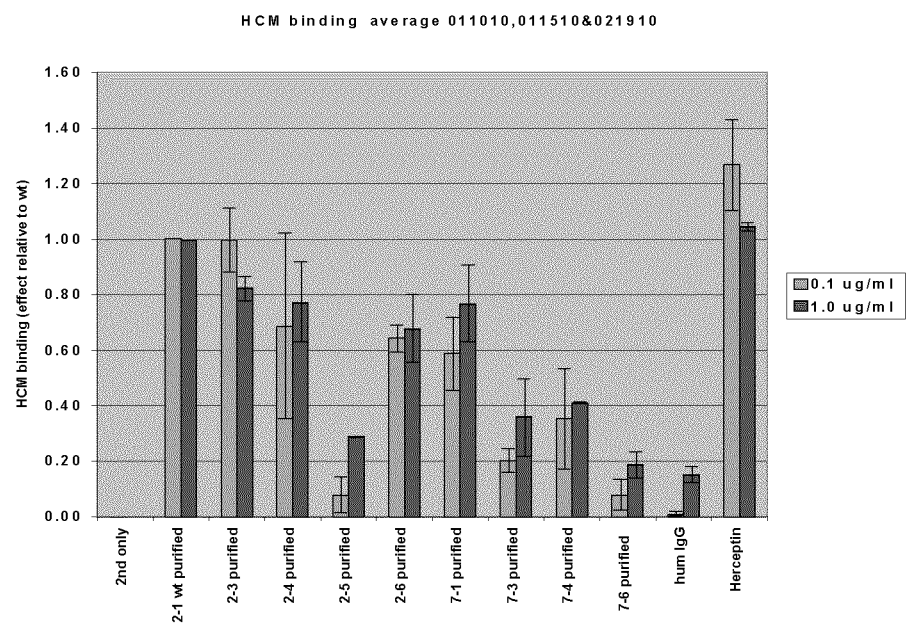

Figure 2 A&B
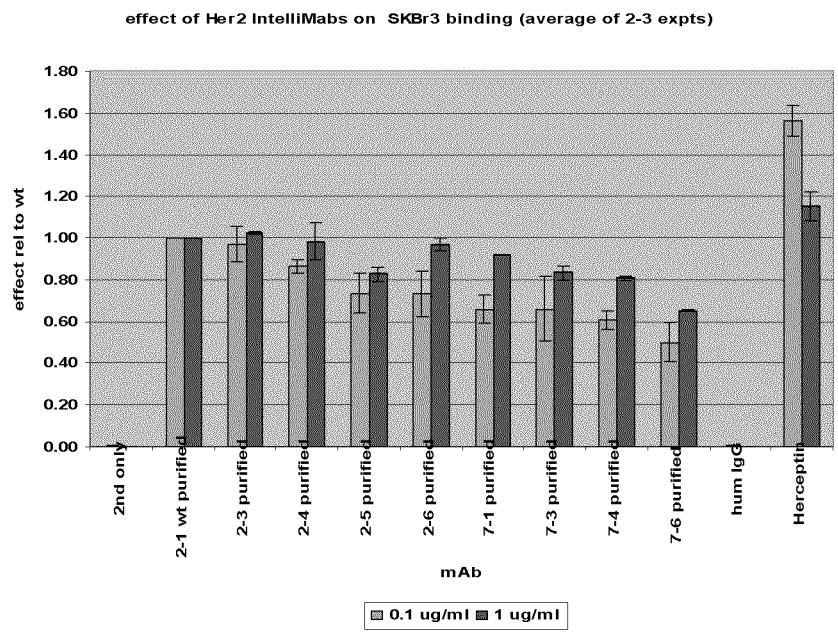
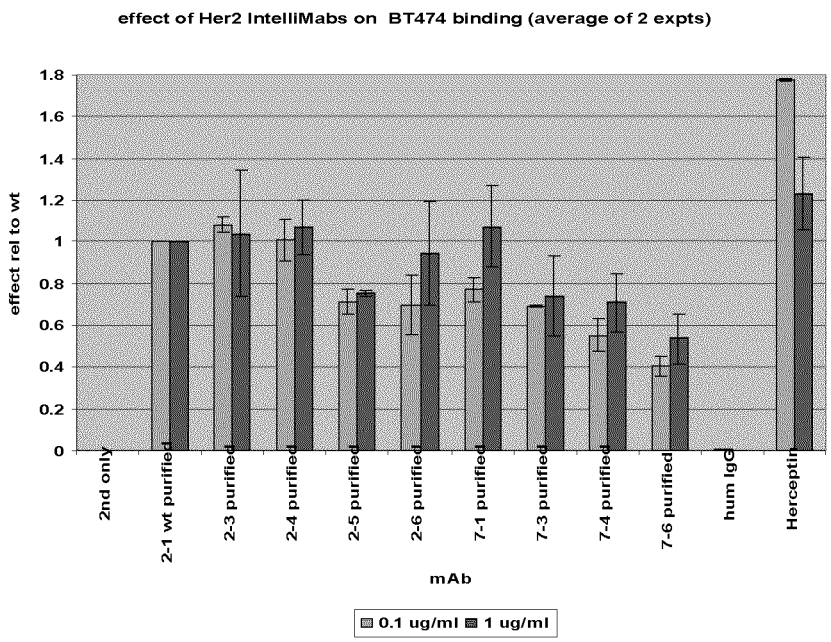

ANTIBODIES SELECTIVE FOR CELLS PRESENTING ERBB2 AT HIGH DENSITY

This application is a national stage application of PCT International Application No. PCT/CA2011/050747, filed Dec. 2, 2011, which claims priority to U.S. Provisional Application Ser. No. 61/419,983, filed Dec. 6, 2010, each of which is incorporated by reference herein in its entirety.

FIELD OF THE INVENTION

This invention relates to antibodies having therapeutic and diagnostic utility. More particularly, the present invention relates to antibodies that bind selectively to cells that present erbB2 at abnormally high density. The antibodies are useful therapeutically and diagnostically in the fields of oncology and other diseases.

BACKGROUND TO THE INVENTION

Drugs for the treatment of cancer and other diseases have a so-called "therapeutic window". In the case of cancer, the therapeutic window defines the drug dosage that can kill cancer cells preferentially to normal cells, thereby establishing a safety range for the use of the drug. The therapeutic window for conventional chemotherapeutics is narrow with, in many cases, significant adverse effects coinciding with marginal slowing of tumour growth. Targeted treatments that spare normal cells are urgently needed.

Therapeutic antibodies form a newer class of cancer therapies that specifically target an antigen presented on the surface of cancer cells. When the target surface protein is unique to the cancer cell, adverse antibody effects on normal cells can be avoided. However, for the majority of antigens, target expression is not restricted completely to tumour cells, with some normal cells also expressing the antigen. In these cases, the antibody may have an effect on normal cells as well as tumor cells, leading to "on-target, off-tissue" adverse events. In the case of the ErbB2 antigen, because it is present on the surface of normal cells in cardiac tissue as well as on breast cancer cells, the clinical use of erbB2-targeting therapeutics is associated with adverse events that include cardiac toxicity. The incidence and degree of adverse events is considerably increased when given in combination with chemotherapeutics, particularly anthracyclines.

Considering the efficacy of anti-erbB2 therapies in treating patients that overexpress erbB2, the risk associated with cardiac toxicity is currently considered acceptable when managed properly. The risk of anti-erbB2 therapy-associated cardiac toxicity can be reduced by avoiding co-administration with anthracyclines, or by administering anti-erbB2 therapy and chemotherapeutics consecutively.

Currently, routine LVEF monitoring is performed to assess cardiac function in patients that are prescribed anti-erbB2 therapies, especially when given in combination with anthracyclines. This is a time-consuming and expensive process which requires patient compliance.

Efforts to improve upon erbB2 antibodies are aimed at generating antibodies having even greater affinity for the target antigen. For instance, U.S. Pat. No. 7,435,797 issued Oct. 14, 2008 describes a variety of trastuzumab analogs in which amino acid substitution is used to further increase target affinity. Substitutions are made at sites within different complementarity determining regions of trastuzumab.

It would be desirable to provide an erbB2 antibody that is useful to treat subjects presenting with erbB2 over-expressing disease cells, while avoiding significant interaction with cardiac and other normal cells that also present the erbB2 antigen.

It is an object of the present invention to provide therapeutic antibodies, and fragments and conjugates thereof that bind effectively to a given target only when that target is presented at a relatively higher density characteristic of a disease state.

It is a further object of the present invention to provide such antibodies, fragments and conjugates in pharmaceutical compositions, particularly for therapeutic and diagnostic use.

It is a further object of the present invention to provide a method useful, in a subject in need thereof, to control the growth of disease cells that present erbB2 at a density greater than normal erbB2 density, while avoiding or minimizing adverse effects on normal cells.

SUMMARY OF THE INVENTION

In one aspect, the present invention provides an isolated, erbB2 antibody or bivalent fragment thereof that binds preferentially to target cells that present erbB2 at a density above a normal erbB2 density. Cells that present erbB2 at a density greater than normal erbB2 density are disease cells, including cancer cells such as breast cancer cells, that over-express the her-2 gene, and manifest on their surface a greater number of erbB2 proteins than cells that express the her-2 gene at normal levels.

The antibodies of the present invention, and their bivalent fragments, display a preference for binding to disease cells having the higher erbB2 density, and show reduced and desirably minimal or negligible binding to normal cells having a normal erbB2 density. The present antibodies and their bivalent binding fragments thus are well suited for use in reducing or eradicating high density erbB2 disease cells while minimizing or avoiding effects on normal cells, thereby reducing adverse events in subjects receiving erbB2 antibody therapy.

In one aspect, the erbB2 antibody comprises a heavy chain and a light chain, each chain having a constant region and a variable region, each variable region comprising framework regions and complementarity determining regions (CDRs), wherein the CDRs have an amino acid sequence set forth below:

```
For the heavy chain:
CDR1
                                    (SEQ ID No. 1)
GFNIKDTYIH For the light chain:
CDR2
                                    (SEQ ID No. 2)
RIYPTNGY57TR59YADSVKG CDR3
                                    (SEQ ID No. 3)
WGGDGFYAMDY
``` wherein at least one of Y57, R59, N30, F53, and Y92 is replaced by a substituting amino acid that reduces the erbB2 binding affinity of said antibody. In embodiments, the substituting amino acid(s) are selected to confer on the antibody a binding affinity (KD) for erbB2 that is about 10 fold or more weaker than the erbB2 binding affinity of trastuzumab.

In embodiments, the present invention provides an ErbB2 antibody comprising a heavy chain and a light chain, each chain having a constant region and a variable region, wherein the light chain variable region comprise the sequence of SEQ ID No. 7 and the heavy chain variable region comprises the sequence of SEQ ID No. 8, wherein at least one of Y57, R59, N30, F53, and Y92 is replaced by a substituting amino acid that reduces the erbB2 binding affinity of said antibody.

In other embodiments, the substituting amino acid is selected to reduce erbB2 binding affinity of the antibody or bivalent fragment to a level that substantially eliminates binding to cells presenting erbB2 at a normal erbB2 density, and retains effective binding at targeted disease cells that present erbB2 at a greater density relative to normal cell erbB2 density.

In still other embodiments, the antibody or bivalent fragment is a variant of trastuzumab having one or more substitutions at the residues identified herein.

In another of its aspects, the present invention provides conjugates, i.e., immunoconjugates, comprising an antibody or bivalent fragment thereof according to the present invention and, conjugated therewith, an agent useful to treat or diagnose cells presenting erbB2 at a density characteristic of disease cells.

In a further aspect, the present invention provides medically useful compositions comprising an antibody, bivalent fragment thereof or immunoconjugate thereof according to the present invention, in combination with a medically acceptable carrier, such as a pharmaceutically acceptable carrier or a diagnostically useful carrier.

In a related aspect, the present invention provides a method for treating a subject having disease cells that present erbB2 at a density greater than the erbB2 density on normal cells, comprising the step of administering to the subject an effective amount of an antibody, bivalent fragment thereof, or an immunoconjugate of the present invention. Subjects so treated will manifest adverse events that are fewer in number and/or severity given the reduced affinity of the present antibodies for normal cells and tissue.

These and other aspects of the present invention are now described in greater detail with reference to the accompanying drawings, in which:

REFERENCE TO THE FIGURES

Figure 1:
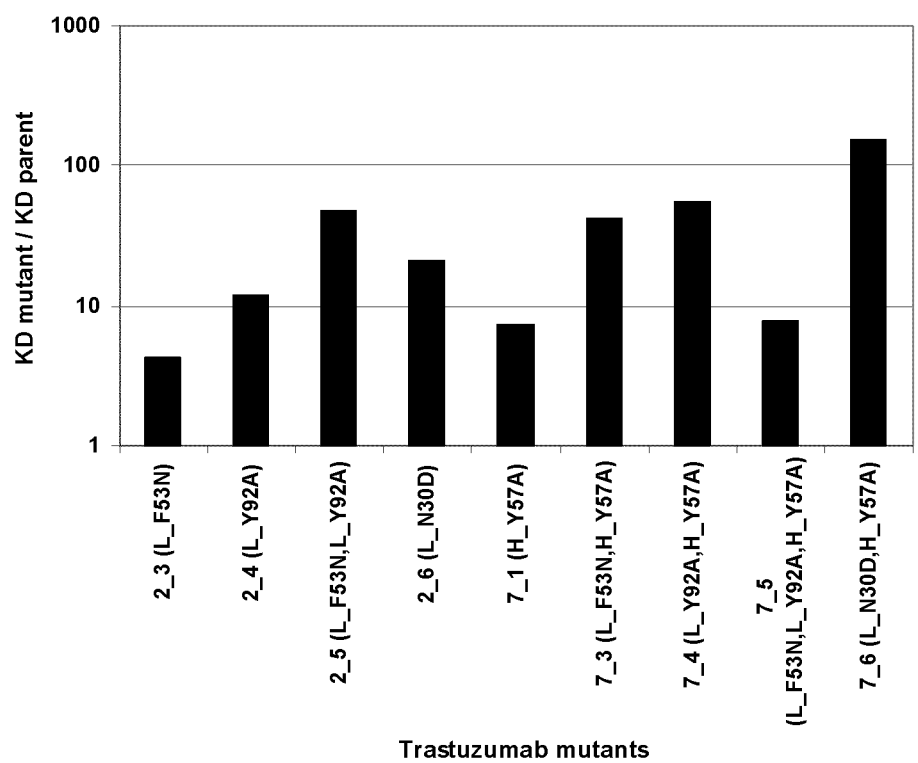
Figure 3:
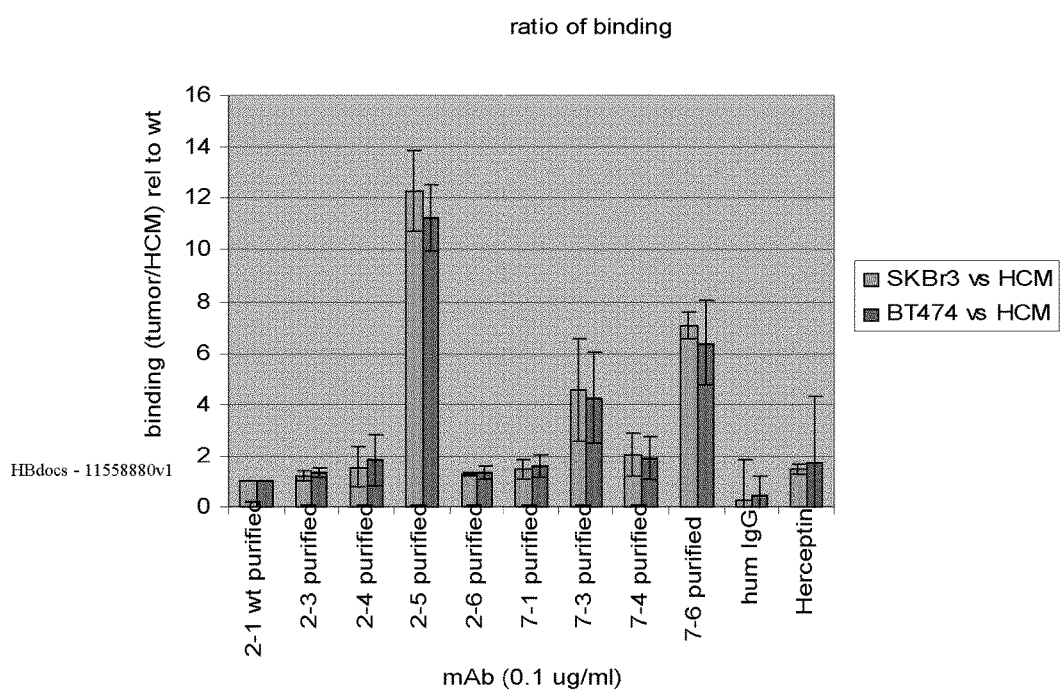

FIG. 1 shows the in vitro effect of substitution on antibody affinity for erbB2;

FIG. 2 is a graph showing binding of antibodies to cell surface erbB2 present on tumour cells (A) SkBr3, (B) BT474, and (C) human cardiac myocytes (HCM) at 0.1 and 1 ug/ml mAb, and compared to wt mAb (2-1 wt, set arbitrarily to 100%); and FIG. 3 is a graph representing binding selectivity of antibodies. The ratio of antibody binding to SKBr3 cells or BT474 cells (overexpressing erbB2) divided by their respective binding to normal HCM (at 0.1 mg/ml) was calculated and compared to that seen with 2-1 wild type antibody (set arbitrarily to 1).

DETAILED DESCRIPTION OF THE INVENTION AND PREFERRED EMBODIMENTS

As used herein, the term "erbB2" refers to any protein that comprises the expressed and processed product of the her-2 gene, wherein the protein is designated as UniProtKB/ Swiss-Prot P04626-1, including antibody-binding variants thereof.

The present invention relates to erbB2 antibodies and bivalent fragments thereof that display a preference for binding to disease cells presenting erbB2 at a density greater than normal cells. On cells that present erbB2, the normal density of erbB2 is generally less than about 10,000 erbB2 molecules per cell, and is usually less than about 1,000 erbB2 molecules per cell. ErbB2-presenting disease cells, on the other hand, present erbB2 at a density generally greater than 10,000 erbB2 molecules per cell, and usually greater than about 100,000 erbB2 molecules per cell. Generally, the erbB2 density is thus about $10^3$ or less on normal cells, and about $10^5$ or more on disease cells. The actual number of erbB2 molecules on any given cell can be determined by established methods, including the antibody based radiolabeled binding or flow cytometry binding to live cells herein exemplified. The binding avidity of the present antibodies is greater for the higher erbB2 density disease cells than for the lower erbB2 density normal cells. This greater avidity is revealed conveniently using techniques established for determining affinity constants for antibody-target interactions, also as exemplified herein.

In embodiments, the present erbB2 antibodies have a binding affinity for erbB2 that is about 10 fold or more weaker than the erbB2 binding affinity of trastuzumab. Desirably, the binding affinity of the antibody for erbB2 is about 15-fold, 20-fold, 25-fold, and preferably 30-fold or more weaker than the erbB2 binding affinity of trastuzumab. In absolute terms, and given an erbB2 binding affinity of about 0.03 nM for trastuzumab, the present antibodies incorporate amino acid substitution(s) that reduce their erbB2 binding affinity to about 0.1 nM and weaker, e.g., to an erbB2 binding affinity that is in the range from 0.1 nM to 100 nM, more desirably 0.5 nM to 100 nM, such as 0.7 nM to 100 nM, or 1 nM to 100 nM, or 1 nM to 75 nM, or 1 nM to 50 nM, or 1 nM to 25 nM, or 1 nM to 10 nM, or 1 nM to 5 nM.

In embodiments, the antibody is an intact antibody comprising features common to all natural antibodies, and thus comprises a heavy chain and a light chain, each chain having a constant region and a variable region, each variable region comprising framework regions (FRs) and complementarity determining regions (CDRs). In the alternative, the antibody is provided as a bivalent fragment, i.e., an antibody fragment comprising both "arms" of an intact antibody, joined through a linker that can be represented by the hinge region of the antibody or any equivalent. Such bivalent fragments include $F(ab)_2$ fragments and any other bivalent fragment that retains preference for high density erbB2. In particular embodiments, the bivalent fragment is a $F(ab')_2$ fragment, generated for instance by papain-based digestion of the parent antibody using standard procedures for digestion and subsequent fragment isolation. In the alternative, the bivalent fragment can be a so-called single chain Fv (scFv), consisting of the variable light and variable heavy antibody domains joined by an amino acid linker, or a bivalent form of a so-called diabody prepared using a 5 amino acid linker such as SGGGG between the light and heavy chain variable domains and a C-terminal cysteine modification to GGC to give a final diabody product as VL-SGGG-VH-GGC. Still other bivalent fragments can be prepared by coupling the light and heavy chain variable domains through thioether linkages such as bis-maleimidomethyl ether (BMME), N,N'-p-phenylene dimaleimide (PDM and N,N'-bismaleimido-hexane BMH), to stabilize the F(ab')2 fragments.

In the intact antibody or bivalent fragment, the CDRs comprise or consist of the following amino acid sequences:

For the heavy chain:
CDR1
GFNIKDTYIH (SEQ ID No. 1)

CDR2
RIYPTNGY$^{57}$TR$^{59}$YADSVKG (SEQ ID No. 2)

CDR3
WGGDGFYAMDY (SEQ ID No. 3)

For the light chain:
CDR1
RASQDVN$^{30}$TAVA (SEQ ID No. 4)

CDR2
SASF$^{53}$LYS (SEQ ID No. 5)

CDR3
QQHY$^{92}$TTPPT (SEQ ID No. 6)

wherein at least one of Y57, R59, N30, F53, and Y92 is replaced by a substituting amino acid that reduces the erbB2 binding affinity of said antibody or bivalent fragment.

The substituting amino acids are most suitably genetically encoded amino acids that are selected desirably, but not essentially, from an amino acid class that is different from the amino acid class to which the parent amino acid belongs. For instance, in the case of Y57, suitable substituting amino acids are those that are not polar/neutral/large amino acids. The selection process can be conducted by applying computer aided tools that couple saturation virtual mutagenesis engines with algorithms for in silico scoring of binding affinities and/or association rates. Amino acid selections can also be made based on the following Table 1:

| Amino Acid | 3 letter | 1 letter | Polarity (side chain) | Charge (pH 7.4) | Size* |
|---|---|---|---|---|---|
| Alanine | Ala | A | nonpolar | neutral | tiny |
| Arginine | Arg | R | polar | positive | large |
| Asparagine | Asn | N | polar | neutral | small |
| Aspartic acid | Asp | D | polar | negative | small |
| Cysteine | Cys | C | nonpolar | neutral | small |
| Glutamic acid | Glu | E | polar | negative | small |
| Glutamine | Gln | Q | polar | neutral | small |
| Glycine | Gly | G | nonpolar | neutral | tiny |
| Histidine | His | H | polar | neutral (90%) | large |
| Isoleucine | Ile | I | nonpolar | neutral | large |
| Leucine | Leu | L | nonpolar | neutral | large |
| Lysine | Lys | K | polar | positive | large |
| Methionine | Met | M | nonpolar | neutral | large |
| Phenylalanine | Phe | F | nonpolar | neutral | large |
| Proline | Pro | P | non-polar | neutral | small |
| Serine | Ser | S | polar | neutral | tiny |
| Threonine | Thr | T | polar | neutral | small |
| Tryptophan | Trp | W | nonpolar | neutral | bulky |
| Tyrosine | Tyr | Y | polar | neutral | large |
| Valine | Val | V | nonpolar | neutral | small |

*based on volume in $Å^3$, where 50-100 is tiny, 100-150 is small, 150-200 is large and >200 is bulky In embodiments, the heavy chain variable region of the antibody or bivalent fragment incorporates at least one substitution at Y57 or R59. In other embodiments, the heavy chain variable region incorporates substitutions at both Y57 and R59. In an alternative embodiment, the heavy chain variable region is wild type and incorporates no such substitutions, provided there is at least one substitution and optionally two substitutions in the light chain variable region.

In embodiments, Y57 is replaced by a substituting amino acid having a side chain that is nonpolar and/or a side chain that is non-neutral and/or a side chain that is not large. Desirably, Y57 is replaced by an amino acid selected from A, C, G, I, L, M, F, W and V; preferably from A, G, I, L and V; and more preferably from A, V, I and L. In a specific embodiment, Y57 is replaced by A57, thus yielding the substitution designated Y57A.

In other embodiments, R59 is replaced by a substituting amino acid having a side chain that is nonpolar and/or is charge neutral or negative and/or is not large. Desirably, R59 is replaced by an amino acid having a side chain that is charge neutral or negative, as well as polar, as well as small, and is selected desirably from D and E. In a specific embodiment, R59 is replaced by E59, thus yielding the substitution designated R59E.

In embodiments, the light chain variable region of the antibody or bivalent fragment incorporates at least one substitution at N30 or at F53 or at Y92. In other embodiments, when the heavy chain comprises at least one substitution, then the light chain variable region comprises at least two such substitutions, or all three such substitutions. In a specific embodiment, the light chain variable region incorporates substitutions at both F53 and Y92. In another specific embodiment, the light chain variable region incorporates substitution only at N30, only at F53 or only at Y92. In an alternative embodiment, the light chain variable region is wild type and incorporates no such substitutions, provided there is at least one substitution in the heavy chain variable region.

When substituted, N30 is replaced by a substituting amino acid having a side chain that is either nonpolar and/or is negative or positive in charge and/or may not be small. In embodiments, N30 is substituted by an amino acid that is not S, and is selected from R, D, E, or K. In a preferred embodiment, N30 is substituted by D, yielding the substitution designated N30D.

When substituted, F53 is replaced by a substituting amino acid having a side chain that is either polar and/or is charge positive or negative and/or is not large. In embodiments, F53 is replaced by R, N, D, E, Q, H, K, S, T or Y. In particular embodiments, F53 is replaced by N, Q, H, S, T or Y. In a preferred embodiment, F53 is replaced by N, yielding the substitution designated F53N.

When substituted, Y92 is replaced by a substituting amino acid having a side chain that is nonpolar and/or a side chain that is non-neutral and/or is not large. Desirably, Y92 is replaced by an amino acid selected from A, C, G, I, L, M, F, W and V; preferably from A, G, I, L and V; and more preferably from A, V, I and L. In a specific embodiment, Y92 is replaced by A92, thus yielding the substitution designated Y92A.

The antibody or bivalent fragment thereof comprises at least one substitution at a location noted above. The at least one substitution can occur in either the light chain variable region or the heavy chain variable region. In embodiments, and in the case where there is a single substitution that is only within the antibody light chain, that substitution is other than N30A, F53N, Y92A and Y92F.

In other embodiments, the antibody or binding fragment thereof comprises at least two such substitutions, either both in the light chain variable region, both in the heavy chain variable region, or at least one substitution in each of the light and heavy chain variable regions. In specific embodiments, the light chain variable region and the heavy chain variable region incorporate substitutions as follows:

TABLE 2

| Light Chain | Heavy chain | | |
| --- | --- | --- | --- |
| | Wild type | Y57A | R59E |
| Wild type | — | wt, Y57A | wt, R59E |
| N30D | N30D, wt | N30D, Y57A | N30D, R59E |
| F53N | F53N, wt | F53N, Y57A | F53N, R59E |
| Y92A | Y92A, wt | Y92A, Y57A | Y92A, R59E |
| F53N&Y92A | F53N&Y92A, wt | F53N&Y92A, Y57A | F53N&Y92A, R59E |

In preferred embodiments, the erbB2 antibody incorporates (1) a wild type heavy chain and light chain substitutions of both F53 and Y92, such as F53N and Y92A, or (2) a heavy chain substituted at Y57, such as Y57A, and a light chain substituted at N30, such as N30D.

In addition to the recited three CDRs present in each of the light and heavy chain variable regions, the heavy and light chains of the intact antibody comprise four intervening framework regions that present the CDRs in a conformation suitable for erbB2 binding, and constant regions that confer antibody effector function. The CDRs can be integrated into any suitable acceptor antibody, by grafting the present CDRs into the acceptor antibody, in accordance with practices and techniques well established for the production of chimeric, humanized and human antibodies.

Particularly suitable acceptor antibodies are antibodies already known to have erbB2 binding affinity. Such donor antibodies are most desirably of human origin, but they can also derive from acceptor antibodies of non-human origin, including mouse, rat, rabbit, goat, sheep, primate and the like. It will be appreciated that human antibody acceptor sequences different from those exemplified herein can be identified and used to accommodate the presently desired CDRs. This is achieved by modeling the structure of a preferred antibody using for instance the Swiss-Model [http://swissmodel.expasy.org/repository] or similar software and selecting, from among the numerous human antibody sequences available in public databases, a human acceptor antibody sequence that, with CDR sequences altered as herein preferred, approximates the same structural conformation as the preferred antibodies. In embodiments, the acceptor antibodies, and the resulting present antibodies, are of the IgG1 isotype, but they may also be IgG2 or IgG4. Moreover, the isotype of the antibody, as dictated by the constant region, can be manipulated to alter or eliminate the effector function of the resulting antibody. That is, the constant region of the present antibodies is either wild type human antibody constant region, or a variant thereof that incorporates amino acid modifications, i.e., amino acid additions, substitutions or deletions that alter the effector function of the constant region, such as to enhance serum half-life, reduce complement fixation, reduce antigen-dependent cellular cytotoxicity and improve antibody stability. The number of amino acid modifications in the constant region is usually not more than 20, such as 1-10 e.g., 1-5 modifications, including conservative amino acid substitutions.

In embodiments, the half life of the antibody is improved by incorporating one more amino acid modification, usually in the form of amino acid substitutions, for instance at residue 252, e.g., to introduce Thr, at residue 254, e.g., to introduce Ser, and/or at residue 256 e.g., to introduce Phe. Still other modifications can be made to improve half-life, such as by altering the CH1 or CL region to introduce a salvage receptor motif, such as that found in the two loops of a CH2 domain of an Fc region of an IgG. Such alterations are described for instance in U.S. Pat. No. 5,869,046 and U.S. Pat. No. 6,121,022.

Altered C1q binding, or reduced complement dependent cytotoxicity, can be introduced by altering constant region amino acids at locations 329, 331 and 322, as described in U.S. Pat. No. 6,194,551. The ability of the antibody to fix complement can further be altered by introducing substitutions at positions 231 and 239 of the constant region, as described in WO94/029351.

The framework regions of the light and heavy chains of the present antibodies and fragments also desirably have the sequence of a human antibody variable region, but incorporating the CDRs herein specified. In embodiments, the heavy chain variable region is human IgG4 in origin. In specific embodiments, the heavy chain variable region is that of human IgG, such as the human IgG1 antibody variant having the sequence designated Genbank gi 2414502. Alternatively, and preferably, the heavy chain variable region is that of human IgG4 antibody species designated Genbank gi 2414502.

The framework regions of the heavy and light chains of the present antibodies may also incorporate amino acid modifications, i.e., amino acid deletions, additions or substitutions, which further improve upon the properties of the antibody or fragment, in accordance with techniques established for antibody humanization. Such framework modifications can be modeled on the framework regions of antibody sequences provided in public databases, and on framework regions of antibodies known to bind erbB2, such as those antibodies referenced in the background section hereof. Preferred framework substitutions are those which yield antibodies having a greater preference for binding erbB2 at the higher density associated with disease cells, relative to normal cells.

Framework modifications can also be made to reduce immunogenicity of the antibody or to reduce or remove T cell epitopes that reside therein, as described for instance by Carr et al in US2003/0153043.

In accordance with embodiments of the present invention, the heavy and light chain variable regions are modeled on the antibody trastuzumab, and comprise a light chain variable region of SEQ ID No. 7, and/or a heavy chain variable region having SEQ ID No. 8 as follows:

```
Light chain variable region (VL):
                                                    [SEQ ID No. 7]
DIQMTQSPSSLSASVGDRVTITCRASQDVN30TAVAWYQQKPGKAPKLLIYSASF53LYSGVPS RFSGSRSGTDFTLTISSLQPEDFATYYCQQHY92TTPPTFGQGTKVEIK,
wherein N30, F53, and Y92 are as defined hereinabove;

Heavy chain variable region (VH)
                                                    [SEQ ID No. 8]
EVQLVESGGGLVQPGGSLRLSCAASGFNIKDTYIHWVRQAPGKGLEWVARIYPTNGY57TR59Y ADSVKGRFTISADTSKNTAYLQMNSLRAEDTAVYYCSRWGGDGFYAMDYWGQGTLVTVSS;
wherein Y57 and R59 are as defined hereinabove.
```

In more specific and preferred embodiments, the entire light and heavy chains of the intact antibody are set out below as SEQ ID Nos. 9 and 10, respectively:

```
Entire Light chain
                                                      [SEQ ID No. 9]
DIQMTQSPSSLSASVGDRVTITCRASQDVN30TAVAWYQQKPGKAPKLLIYSASF53LYSGVPS

RFSGSRSGTDFTLTISSLQPEDFATYYCQQHY92TTPPTFGQGTKVEIKRTVAAPSVFIFPP

SDEQLKSGTASVVCLLNNFYPREAKVQWKVDNALQSGNSQESVTEQDSKDSTYSLSSTLT

LSKADYEKHKVYACEVTHQGLSSPVTKSFNRGEC;
wherein N30, F53, and Y92 are as defined hereinabove;

Entire Heavy chain
                                                     [SEQ ID No. 10]
EVQLVESGGGLVQPGGSLRLSCAASGFNIKDTYIHWVRQAPGKGLEWVARIYPTNGY57TR59Y

ADSVKGRFTISADTSKNTAYLQMNSLRAEDTAVYYCSRWGGDGFYAMDYWGQGTLVTVSS

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDTPPPCPRCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPGK;
wherein Y57 and R59 are as defined hereinabove.
```

As noted, final selection of an antibody or binding fragment is made based on the binding preference displayed by the desired antibody or bivalent fragment for cells that present erbB2 at a density greater than normal. The target cells are thus disease cells presenting greater than normal erbB2 density, as a hallmark. Screening can be performed in vitro, as exemplified herein, using as reference cells a first disease cell known from analysis to present erbB2 at a density greater than normal, such as the human breast adenocarcinoma cell line SkBr3 ATCC HTB-30 (~2.5M ErbB2/cell) or the human breast ductal carcinoma cell line BT474 ATCC HTB-20 (~3M Her2/cell) and a second, normal cell known from analysis to present erbB2 at a normal density, such as normal human cardiac myocytes (~20,000 ErbB2/cell). The choice of cardiac myocytes as the reference, normal cell is prudent, given that marketed ErbB2 antibodies, such as trastuzumab, are known to elicit cardiac side effects through their interaction with these cells. Any other human cell line that presents erbB2 at normal density can be used, in the alternative.

The cell-based assay can use flow cytometry with appropriate erbB2 antibody and labeled secondary antibody to report and measure binding affinity and avidity, as exemplified herein. In the alternative, selection of the desired antibody can be performed based on absolute binding affinities obtained for instance using surface plasmon resonance, also as exemplified herein.

For purposes of identifying disease cells that can be targeted by the present erbB2 antibodies and bivalent fragments, the commercial test known as HerceptTest® can conveniently be used. This is a semi-quantitative immunohistochemical assay for determination of her-2 protein overexpression in breast cancer tissues. Positive or negative results aid in the classification of abnormal cells/tissues and provide a basis for treatment with erbB2 antibody.

The antibodies and binding fragments thus are useful for both diagnostic purposes, including sample testing and in vivo imaging, and for therapeutic purposes to treat diseases in which erbB2 density is increased on disease cells.

For either purpose, the antibody or binding fragment can be conjugated to an appropriate agent, to form an immunoconjugate. Agents appropriate for treating disease include cytotoxic agents include chemotherapeutics and radiotherapeutics. For diagnostic purposes, appropriate agents are detectable labels that include radioisotopes, for whole body imaging, and radioisotopes, enzymes, fluorescent labels and the like for sample testing.

For therapy, the cytotoxin may be conjugated with the antibody or bivalent binding fragment through non-covalent interaction, but more desirably, are coupled by covalent linkage either directly or, more preferably, through a suitable linker. In a preferred embodiment, the conjugate comprises a cytotoxin and an antibody. Immunoconjugates of the antibody and cytotoxin are made using a variety of bifunctional protein coupling agents such as N-succinimidyl-3-(2-pyridyldithiol) propionate, iminothiolane, bifunctional derivatives of imidoesters such as dimethyl adipimidate HCL, active esters such as disuccinimidyl suberate, aldehydes such as glutaraldehyde, bis-azido compounds such as bis-(p-diazoniumbenzoyl)-ethylenediamine), diisocyanates such as toluene 2,6-diisocyanate, and bis-active fluorine compounds (such as 1,5-difluoro-2,4-dinitrobenzene). Carbon-14-labeled 1-isothiocyanobenzyl-3-methyldiethylene triaminepentaacetic acid (MX-DTPA) is a chelating agent suitable for conjugation of radio nucleotide to the antibody.

The cytotoxin component of the immunoconjugate can be a chemotherapeutic agent, a toxin such as an enzymatically active toxin of bacterial, fungal, plant or animal origin, or fragments thereof, or a small molecule toxin, or a radioactive isotope such as $^{212}$Bi, $^{131}$I, $^{131}$In, $^{111}$In, $^{90}$Y, and $^{186}$Re, or any other agent that acts to inhibit the growth or proliferation of a cancer cell.

Chemotherapeutic agents useful in the generation of such immunoconjugates include adriamycin, doxorubicin, epirubicin, 5-fluoroouracil, cytosine arabinoside ("Ara-C"), cyclophosphamide, thiotepa, busulfan, cytoxin, taxoids, e.g. paclitaxel, and docetaxel, toxotere, methotraxate, cisplatin, melphalan, vinblastine, bleomycin, etoposide, ifosgamide, mitomycin C, mitoxantrone, vincristine, vinorelbine, carboplatin, teniposide, daunomycin, caminomycin, aminopterin, dactinomycin, mitomycins, esperamicins, 5-FU, 6-thioguanine, 6-mercaptopurine, actinomycin D, VP-16, chlorambucil, melphalan, and other related nitrogen mustards. Also included are hormonal agents that act to regulate or inhibit hormone action on tumors such as tamoxifen and onapristone. Toxins and fragments thereof which can be used include diphtheria A chain, nonbonding active fragments of diphtheria toxin, cholera toxin, botulinus toxin, exotoxin A chain (from *Pseudomonas aeruginosa*), ricin A chain, abrin A chain, modeccin A chain, alpha-sarcin, *Aleurites fordii* proteins, dianthin proteins, phytolaca Americana proteins (PAPI, PAPII, and PAP-S), *momordica charantia* inhibitor, curcin, crotin, sapaonaria, officinalis inhibitor, gelonin, saporin, mitogellin, restrictocin, phenomycin, enomycin, and the tricothcenes. Small molecule toxins include, for example, calicheamicins, maytansinoids, palytoxin and CC1065.

Pharmaceutical Compositions

Therapeutic formulations of the antibody, bivalent fragment or the conjugate are prepared for storage by mixing the antibody or conjugate having the desired degree of purity with optional pharmaceutically acceptable carriers, excipients or stabilizers (Remington's Pharmaceutical Sciences, $16^{th}$ edition, Osol, A. Ed. [1980]), in the form oflyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, or benzyl alcohol; alkyl parabens such as methyl or propyl paraben; catechol; resorcinol; cyclohexanol; 3-pentanol; and m-cresol); low molecular weight (less than about 10 residues) polypeptides; proteins such as serum, albumin, gelatin, or immunoglobulins; hydrophilic polymers such as polyvinylpyrrolidone; amino acids such as glycine, glutamine, asparagines, histidine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS or polyethylene glycol (PEG).

The active ingredients to be used for in vivo administration must be sterile. This is readily accomplished by filtration through sterile filtration membranes.

Sustained-release preparations may be prepared. Suitable examples of sustained-release include semipermeable matrices of solid hydrophobic polymers containing the antibody, which matrices are in the form of shapes articles, e.g., films or microcapsules. Examples of sustained-release matrices include polyesters, hydrogels (for example, poly (2-hydroxyethyl-methacrylate), polyactides (U.S. Pat. No. 3,773, 919), copolymers of L-glutamic acid and ethyl-L-glutamate, non-degradable ethylene-vinyl acetate, degradable lactic acid-glycolic acid copolymers such as injectable microspheres composed of lactic acid-glycolic acid copolymer and leuprolide acetate, and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Pharmaceutical Combinations

Administration "in combination with" one or more further therapeutic agents includes simultaneous (concurrent) and consecutive administration in any order. Other therapeutic regimens may be combined with the administration of the anti-cancer agents, e.g., antibodies or conjugates, of the instant invention. For example, the patient to be treated with such anti-cancer agents may also receive radiation therapy, such as external beam radiation. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration or the anti-tumor agent, e.g., antibody, or may be given simultaneously therewith. The antibody may be combined with an anti-estrogen compound such as tamoxifen or an anti-progesterone such as onapristone (see, EP 616812) in dosages known for such molecules.

It may be desirable to also administer antibodies or conjugates against other tumor associated antigens, such as antibodies which bind to the EGFR, ErbB3, ErbB4, or vascular endothelial factor (VEGF). Alternatively, or in addition, two or more antibodies binding that same or two or more different antigens disclosed herein may be co-administered to the patient. Sometimes it may be beneficial to also administer one or more cytokines to the patient. In a preferred embodiment, the antibodies herein are co-administered with a growth inhibitory agent. For example, the growth inhibitory agent may be administered first, followed by an antibody of the present invention. However, simultaneous administration or administration of the antibody of the present invention first is also contemplated. Suitable dosages for the growth inhibitory agent are those presently used and may be lowered due to combined action (synergy) of the growth inhibitory agent and the antibody herein.

Kits

In another embodiment of the invention, an article of manufacture containing materials useful for the diagnosis or treatment of the disorders described herein is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or vial having a stopper pierceable by a hypodermic injection needle). The label on, or associated with, the container indicates that the composition is used for treating a cancer condition. The article of manufacture may further compromise a second container compromising a pharmaceutically-acceptable buffer, such as phosphate-buffered saline, Ringer's solution and dextrose solution. It may further include other matters desirable from a commercial and use standpoint, including other buffers, diluents, filters, needles, syringes, and package inserts with instructions for use.

Dosing and Administration

An anti-cancer therapeutic according to the invention may be administered with a pharmaceutically-acceptable diluent, carrier, or excipient, in unit dosage form. Any appropriate route of administration can be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration.

For the treatment of subjects presenting with cancer cells presenting erbB2 at greater density than normal cells, the appropriate dosage of an anti-tumor agent, e.g., an antibody, fragment or conjugate, will depend on the type of disease to be treated, as defined above, the severity and course of the disease, whether the agent is administered for preventative or therapeutic purposes, previous therapy, the patients clinical history and response to the agent, and the discretion of the attending physician. The agent is suitably administered to the patient at one time or over a series of treatments. For example, depending on the type and severity of the disease, about 1 µg/kg to 15 mg/kg (e.g., 0.1-20 mg/kg) of antibody or conjugate is a candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

It will thus be appreciated that an effective amount of the antibody, fragment or immunoconjugate is an amount effective alone or as part of a treatment regimen that retards or inhibits the growth or proliferation of disease cells presenting with higher than normal erbB2 density.

In embodiments, the present antibodies are administered by intravenous infusion, such as at an initial dose of 4 mg/kg over 90 minutes, then 2 mg/kg over 30 minutes, once weekly for 52 weeks, with follow up as required.

The antibody and bivalent fragments are useful in the treatment of a variety of cancers, to inhibit the growth or proliferation of cancer cells and tumours comprising them, including hematopoietic cell cancers and solid tumours. Conditions or disorders to be treated include benign or malignant tumors (e.g., renal, liver, kidney, bladder, breast, gastric, ovarian, colorectal, prostate, pancreatic, lung, vulva, and thyroid); hepatic carcinomas; sarcomas; glioblastomas; and various head and neck tumors; leukemias and lymphoid malignancies. In particular embodiments, the antibody or bivalent fragment are used in the treatment of such cancer cells that express high density erbB2, as determined by the screening assays herein described. In particular embodiments, the cancer cells are erbB2-presenting breast cancer cells.

It will be appreciated that subjects who could benefit from the present method include mammals including humans as well as livestock, and pets.

Screening for High Density erbB2 Cancer Cells

Antibodies and bivalent fragments thereof that bind selectively to the target antigen, e.g. erbB2, are used, in accordance with an aspect of the invention, to screen cancer cells to detect those which present the erbB2 antigen at high density. In a preferred embodiment, screening is applied to a sample of cancer cells taken from a subject that is a candidate for erbB2 antibody therapy. Subjects testing positive for cancer cells that present the erbB2 antigen at high density can then be scheduled for therapy with the present antibody or fragment, or an immunoconjugate thereof. Standard techniques, combined with the antibodies or other binding agents herein described can be used to screen cancer cells. Desirably, the antibodies incorporate a detectable label. The label may be detectable by itself (e.g., radioisotope labels or fluorescent labels) or, in the case of an enzymatic label, may catalyze chemical alteration of a substrate compound or composition which is detectable. Radionuclides that can serve as detectable labels include, for example, I-131, I-123, I-125, Y-90, Re-188, Re-186, At-211, Cu-67, Bi-212, and Pd-109.

In situ detection of the binding to cancer cells bearing high density erbB2 can be performed, using the present antibody or fragment, by immunofluorescence or immunoelectron microscopy. For this purpose, a histological specimen is removed from the patient, and a labeled antibody is applied to it, preferably by overlaying the antibody on a biological sample. This procedure also allows for distribution of the erbB2 antigen to be examined within biopsied tumour tissue, to reveal only those sites at which the antigen is presented at a density higher than normal. It will be apparent for those skilled in the art that a wide variety of histological methods are readily available for in situ detection.

More particularly, erbB2 antibodies or binding fragments may be used to monitor the presence or absence of antibody reactivity in a biological sample (e.g., a tissue biopsy, a cell, or fluid) using standard detection assays. Immunological assays may involve direct detection, and are particularly suited for screening large amounts of samples for the presence of erbB2 positive cancer cells. For example, antibodies may be used in any standard immunoassay format (e.g., ELISA, Western blot, immunoprecipitation, flow cytometry or RIA assay) to measure complex formation. Any appropriate label which may be directly or indirectly visualized may be utilized in these detection assays including, without limitation, any radioactive, fluorescent, chromogenic (e.g., alkaline phosphatase or horseradish peroxidase), or chemiluminescent label, or hapten (for example, digoxigenin or biotin) which may be visualized using a labeled, hapten-specific antibody or other binding partner (e.g., avidin). Exemplary immunoassays are described, e.g., in Ausubel et al., supra, Harlow and Lane, Antibodies: A Laboratory Approach, Cold Spring Harbor Laboratory, New York (1988), and Moynagh and Schimmel, Nature 400:105, 1999. For example, using the antibodies described herein, high density erbB2 is readily detected at the cell surface using standard flow cytometry methods. Samples found to contain increased levels of labeled complex compared to appropriate control samples are taken as indicating the presence of high density erbB2, and are thus indicative of a cancer or other disease amenable to treatment with the present antibodies.

The present antibody is produced suitably by recombinant DNA means, as exemplified herein. For production, there is provided a DNA molecule that encodes the heavy chain of the present antibody, and a DNA molecule that encodes the light chain thereof. The DNA further encodes any suitable signal peptide suitable for expression of a secretable chain precursor that enables proper externalization with folding and disulfide formation to elaborate the desired antibody as a secreted, dimerized and processed protein. To this end, the present invention provides, in one embodiment, a polynucleotide comprising a sequence that encodes the variable region of the light chain of a presently preferred erbB2 antibody, as set out in SEQ ID No. 9, supra. Also provided, in another embodiment, is a polynucleotide comprising a sequence that encodes the variable region of the heavy chain of a presently preferred erbB2 antibody, as set out in SEQ ID No. 10, supra.

In more specific embodiments, the present invention provides a polynucleotide that encodes the entire light chain (SEQ ID No. 11) and the entire heavy chain (SEQ ID No.12) of a preferred erbB2 antibody of the present invention. These sequences are provided at the end of this disclosure.

It will be appreciated that polynucleotide equivalents also can be used, in which synonymous codons are replaced within the sequences provided, to produce the present antibodies.

In embodiments, there are also provided vectors that comprise polynucleotides that encode the heavy chain or the variable region thereof and that encode the light chain or the variable region thereof. To express the antibodies, the polynucleotides are incorporated operably within expression vectors, i.e., operatively linked to transcriptional and translational control sequences. Expression vectors include plasmids, retroviruses, cosmids, and the like. The expression vector and expression control sequences are chosen to be compatible with the expression host cell used. The antibody light chain gene and the antibody heavy gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human CH or CL immunoglobulin sequence, with appropriate restriction sites engineered so that any VH or VL sequence can be easily inserted and expressed, as described above. In such vectors, splicing usually occurs between the splice donor site in the inserted J region, and the splice acceptor site preceding the human C region, and also at the splice regions that occur within the human CH exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

Polynucleotides encoding the heavy chain and/or the light chain, and vectors comprising these can be used for transformation of a suitable mammalian host cell. Methods for introduction of heterologous polynucleotides into mammalian calls include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, polynucleotides may be introduced into mammalian cells by viral vectors. Mammalian cell lines useful as hosts for expression of the antibody-encoding polynucleotides include many immortalized cell lines available from the American Type Culture Collection (ATCC). These include, inter alia, Chine hamster ovary (CHO) cells, NSO, SP2 cells, HeLa cells, baby hamster kidney (BHK) cells, monkey kidney cells (COS, human hepatocellular carcinoma cells (e.g., Hep G2), A549 cells, 3T3 cells, and a number of other cell lines. Mammalian host cells include human, mouse, rat, dog, monkey, pig, goat, bovine, horse, and hamster cells. Cell lines of particular preference are selected through determining which cell lines have high expression levels. Other cell lines that may be used are insect cell lines, such as S19 cells, amphibian cells, bacterial cells, plant cells and fungal cells. When recombinant expression vectors encoding the heavy chain or antigen-binding portion thereof are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. It is likely that antibodies expressed by different cell lines or in transgenic animals will have different glycosylation from each other. However, all antibodies encoded by the polynucleotides provided herein, or comprising the amino acid sequences provided herein are part of the instant invention.

Embodiments are now described in the following examples.

EXAMPLES

The structure of trastuzumab bound to erbB2 [RefTS1] was used as starting point for mutant design. Mutations were introduced only in the CDR regions of the light and heavy chain. First, single-point mutations were generated and evaluated computationally. Virtual mutagenesis was carried out with optional conformational relaxation upon mutation by means of conformational sampling algorithms, such as Monte Carlo minimization [Ref TS2]. Prediction of antigen-antibody relative binding affinities between parent and mutant antibodies was carried out with binding affinity scoring functions, such as the solvated interaction energy (SIE) function [Ref TS3]. Prediction of relative antigen-antibody association rates ($k_{on}$) between parent and mutant antibodies was carried out with methods that evaluate long-range electrostatic interactions, such as HyPARE [Ref TS4]. Candidate single-point mutants were the assembled into multiple-point mutants and re-scored for relative binding affinity.

Multiple-point mutants were generated by combining single-point mutants between light and heavy chains to achieve the targeted change in affinity. A requirement was to use as few single-point mutants as possible and to maximize the number of generated assembled antibodies. Another desirable feature was to generate a pool of mutants with reduced affinities due to either increased dissociation rates ($k_{-off}$) or to decreased association rates ($k_{-on}$). Among suitable candidate single-point mutations, those targeting distinct locations within the antibody-antigen interface, preferably at its periphery, were given higher priority.

Preparation of Plasmids

All the cDNAs encoding the heavy and light chains of the antibodies were ordered from GeneArt (Regensburg Germany). The cDNAs were removed from the plasmid provided by GeneArt by digestion with HindIII and cloned into the HindIII site of plasmid pKCRS previously dephosphorylated with calf intestinal phosphatase (NEB) to prevent recircularization. In pKCRS, transcription of the cDNA is under the control of the strong CR5 promoter, part of the cumate gene switch. The plasmid pKCRS is available from the Biotechnology Research Institute, Montreal, Canada and is described by Mullick et al, BMC Biotechnol., 2006, 6:43. This 3.9 kb plasmid incorporates a HindIII in proper contex with the CR5 promoter and a rabbit b-globin polyA, together with a B-lactamase gene for selection, and colE1 and f1 origins of replication. For transfection of CHO cells, all plasmids were isolated from large culture of *E. coli* using the Plasmid Maxi kit (Qiagen Inc, Mississauga, ON) according to the manufacturer's recommendation. Briefly, 3 ml of LB medium containing 100 μg/ml ampicillin were inoculated with a single colony of *E. coli* and grown for 6 h at 37° C. with vigorous shaking (250 RPM). This preculture was then used to inoculate 250 ml of LB medium containing 100 μg/ml ampicillin. The culture was incubated overnight at 37° C. with vigorous shaking (250 RPM). The bacteria were pelleted by centrifugation at 6000×g, for 15 min, at 4° C. and the plasmid was isolated using the protocols, buffers and columns provided by the kit. The pure plasmids was resuspended in sterile 50 mM TRIS, pH 8 and quantified by measuring the optical density at 260 nm.

Cell Line (CHO-cTA; Clone 5F1) and Growth Conditions

The CHO-cTA cell line (Gaillet, B. et al, *Biotechnol. Prog.* 23:200-209; Mullick, A., et al. *BMC Biotechnol.* 2006, 6:43.) used for transient transfection is a Chinese Hamster Ovary cell line (CHO) adapted to grow in suspension and in protein-free medium. The cell line stably expresses the cumate transactivator (cTA) which activates transcription by binding to the CR5 promoter. The CHO-cTA are maintained in CD-CHO medium (Invitrogen, CDCHO 10743), supplemented with 4 mM glutamine, 50 μg/mL and dextran sulfate (Amersham Pharmacia Biotech) at 37° C. under an atmosphere of 5% $CO_2$. When the cells reach a concentration of $1.0\times10^6$ cells/ml (on average three times a week) they are passaged by diluting them to a concentration of $5.0\times10^4$ cells/ml using fresh medium.

Transient Transfection of CHO-cTA

Before transfection, the cells were washed with PBS and resuspended at a concentration of $2.5\times10^6$ cell/ml in growth medium without dextran sulfate for 3 hrs in suspension culture. 50 ml of cells were transfected by adding slowly 2.5 ml of a CDCHO medium supplemented with 1 μg/ml of plasmid and 5 μg/ml. polyethylenimine (PEI Max; Polysciences). After 2 hrs, the cells were transferred at 30° C. The next days, 50 μg/mL of dextran sulfate was added to the cells and they were incubated at 30° C. for a total of 4 days. The supernatant was clarified by centrifugation and filtered through a 0.22 μM filter and transferred at −80° C. until further analysis.

Polyacrylamide Gel Electrophoresis (SDS-PAGE)

Known amounts of supernatant were resuspended into an equal volume of Laemmli 2× and heated at 95° C. for 5 min and chilled on ice. The samples were then separated on a polyacrylamide Novex 10% Tris-Glycine gel (Invitrogen Canada Inc., Burlington, ON). A standard curve was made by adding known amount of purified human IgG. The gel was then stained using a solution of Coomassie Fluor™-Orange (Molecular Probes, Eugene Oreg.) according to the manufacturer's recommendations. The signal was visualized and quantified using the Typhoon Scanner.

Western Blot Analysis

Known amounts of supernatant were separated on a SDS-PAGE as described above and then transferred onto a Hybond-N nitrocellulose membrane (Amersham Bioscience Corp., Baie d'Urfée, QC) for 1 h at 275 mA. The membrane was blocked for 1 h in 0.15% Tween 20, 5% skimmed milk in PBS and incubated for 1 h with an anti-human IgG conjugated to Cy5 (Jackson, Cat#109-176-099). The signal was revealed by scanning with the Typhoon Trio+ (Amersham Biosciences, GE Healthcare).

ELISA 96 wells/plates were coated with 50 μl of AffiniPure Goat Anti-Human IgG, (H+L) (Jackson Immuno Research) and incubated overnight at 4° C. The wells were washed with PBS and incubated for 30 min at 37° C. with 100 μl of 1% BSA in PBS at 37° C. 25 μl of samples diluted with 1% BSA in PBS were added to the wells, which were incubated for 2 hrs at 37° C. The wells were washed with 0.05% Tween 20 in PBS and incubated with an alkaline Phosphatase-conjugated AffiniPure Goat Anti-Human IgG (H+L) (Jackson Immuno Research) for 1 hr at 37° C. The wells were washed with 0.05% Tween 20 in PBS, followed by PBS. The signal was revealed by incubation with PNPP for 30 min at 37° C. The signal intensity was measure at 405 nm. A standard curve was made using known amount of purified antibody (IgG1, kappa from myeloma plasma (Athens Research Technology).

Purification of Antibody

The supernatant was concentrated with a Amicon Ultra (Ultracel-50K) at 1500 rpm to a volume of 500 μl. The wild type and mutant antibodies were purified using the Nab spin kit Protein A mini column (Thermo Scientific) according to the manufacture's recommendations. The purified antibodies were then desalted and resuspended in PBS using the desalting column PD-10 (GE Healthcare). The antibodies were then concentrated by centrifugation on an Amica Ultra 100,000 MWCO membrane. The purified antibodies were quantified by reading the optical density at 280 nm using the Nanodrop spectrophotometer. The purified antibodies were kept frozen at −20° C. in 50% glycerol.

In Vitro Binding by Surface Plasmon Resonance

Kinetic and affinity analysis was carried out using a BioRad Proteon surface plasmon resonance instrument. The running buffer for all steps was 10 mM HEPES, 150 mM NaCl, 3.5 mM EDTA and 0.05% Tween20 at pH 7.4. An antibody capture sensorchip was prepared by injecting 6.5 ug/mL of anti-mouse Fc (Jackson Immunochemicals Inc.) in 10 mM sodium acetate pH 4.5 at flow rate 25 uL/minute over a GLM sensorchip (BioRad Inc.) that had previously been activated with a 1/10 dilution of sNHS/EDC (BioRad Inc.) until the surface was saturated (approximately 5000 RUs). This procedure was carried out in the analyte direction to ensure all of the interspots for referencing have immobilized anti-mouse Fc. Wild-type trastuzumab and variants was captured in the ligand direction by injecting 100 uL of 4% culture supernatants or purified samples in running buffer at flow rate of 25 uL/min until 400 to 800 resonance units have been captured. This was immediately followed by two pulses of running buffer in the analyte direction, 50 uL each at flow rate 100 uL/min to stabilize the baseline. Next, the simultaneous injection of 100 uL of five ErbB2 (eBiosciences Inc.) concentrations (3-fold dilutions of 30 nM or 20 nM ErbB2) and buffer blank at a flow rate of 50 uL/min with a 600 s dissociation was carried out to analyse the ErbB2—antibody interaction. Kinetic rate constants (on- and off-rates) and affinity constants were generated from the aligned and double referenced sensorgrams with the Langmuir binding model using BioRad Proteon Manager software v3.2.

Cell Culture

The SkBr3 and BT474 cell lines were obtained from ATCC. Cell lines were maintained in DMEM (source) containing 10% fetal bovine serum (Gibco). Primary adult human cardiac myocytes (HCM) were obtained from SciencCell (Catalog #6200) and cultured using manufacturer's recommended Cardiac Myocyte Medium. Generally cells were passaged once or twice a week and used within 4-6 weeks for all experiments.

Detection of Antibody Binding to Surface erbB2 Level by Flow Cytometry

Prior to analysis, cells were plated such that they were not more than 80% confluent on the day of analysis. Tumor cells overexpressing her-2(SkBr3, ~2.5M Her2/cell or BT474, ~3M Her2/cell) or normal (human cardiac myocytes, ~20,000 Her2/cell) were washed in PBS and harvested by the addition of cell dissociation buffer (Sigma.). A cell suspension containing $2.5 \times 10^5$ in 500 µl corresponding cell culture media) was incubated with various concentrations (0.01-100 ug/ml) of anti-HER2 antibodies for 2 h at 4° C. (to prevent internalization). Following 1 wash with cell culture media, primary antibody was incubated with 2 ug Dylight 488 conjugated AffiniPure goat anti-human IgG Alexa 488 secondary antibody (Jackson ImmunoResearch 109-487-003) in 100 ul of media for 1 h at 4° C. Cells were then pelleted and stored on ice until ready to analyzed by flow cytometry. Prior to analysis, cell pellets were resuspended in 300-500 ul media and filtered through a 50 um nylon mesh filter to remove cell aggregates. Flow cytometry analyses were performed on 10,000 viable cells gated on forward scattering, side scattering parameters and propidium iodide dye exclusion using a BD LSRII flow Cytometer (Becton-Dickinson Biosciences, CA, USA) and a standard filter set using BD FACSDiva™ acquisition software, according to manufacturer's instructions.

Specific antibody binding was calculated as the mean fluorescent intensity of binding to each antibody after background level subtraction of the mean fluorescent intensity of binding in the absence of primary antibody (but containing detection antibody). For all experiments, specific antibody binding was compared relative to that of the wild type version of trastuzumab that was produced and purified in the same manner (HC/LC). To examine the binding selectivity of antibodies, the value of antibody binding to tumor (over-expressing ErbB2) was divided by the binding observed with normal human cardiac myocyte cells. This parameter, named the ratio of binding, was calculated and compared to that seen with wild type antibody (named 2-1 wt, set arbitrarily to 1). A commercial source of trastuzumab (Roche) was used as a benchmark for comparison purposes.

Results:

1. Production of ErbB2 Antibodies.

Eight cDNAs corresponding to the coding sequence of the ErbB2 antibodies (Table above) were synthesized (GeneArt). All the cDNAs were cloned into the HindIII site of pKCRS, an expression vector regulated by the cumate-switch (pKCRS vector). For each antibody, 50 ml of CHOcTA (expressing the cumate transactivator, cTA) were transfected with various combinations of heavy and light chain Four days after transfection the supernatant was analyzed by SDS-PAGE (not shown), with quantifications made by Western Blot (Table 4) and by ELISA (Table 3).

TABLE 3

| Heavy and light chains used (Heavy_Light) | Quantification Western blot (mg/L) | Quantification ELISA (mg/L) |
| --- | --- | --- |
| 1_2 | 67.02 | 86.46 |
| 2_3 | 107.27 | 96.79 |

TABLE 3-continued

| | | |
| --- | --- | --- |
| 2_4 | 87.69 | 58.08 |
| 2_5 | 54.36 | 95.51 |
| 2_6 | 26.21 | 22.99 |
| 7_1 | 66.04 | 76.44 |
| 7_3 | 80.14 | 81.98 |
| 7_4 | 60.72 | 118.02 |
| 7_5 | 34.49 | 52.12 |
| 7_6 | 50.10 | 46.45 |
| 8_1 | 81.49 | 66.98 |
| 8_3 | 43.78 | 46.45 |
| 8_4 | 48.22 | 45.98 |
| 8_5 | 48.77 | 61.47 |
| 8_6 | 16.62 | 29.56 |
| K- | 0 | 0 |

Where, for the light chain, and for the heavy chain
1 = wild type light chain    2 = wild type
3 = F53N                     7 = Y57A
4 = Y92A                     8 = R59E
5 = F53N, Y92A
6 = N30D The wild type and 9 mutants were purified by chromatography using protein A. The purified proteins were quantified by $OD_{280}$ (Nanodrop) see Table 4. The purified antibodies were analyzed by non-denaturing and denaturing SDS-PAGE.

TABLE 4

Quantification of the purified antibodies by $OD_{280}$ (Nanodrop)

| Purified mutants | | Concentration (ug/ml) |
| --- | --- | --- |
| 1_2 | Wild type | 580 |
| 2_3 | wt-HC + m1-Lc | 500 |
| 2_4 | wt-HC + m2-LC | 370 |
| 2_5 | wt-HC + m3-LC | 450 |
| 2_6 | wt-HC + -m4-LC | 270 |
| 7_1 | m5-HC + wt-LC | 500 |
| 7_3 | m5-HC + m1-LC | 540 |
| 7_4 | m5-HC + m2-LC | 520 |
| 7_5 | m5-HC + m3-LC | 380 |
| 7_6 | m5-HC + m4-LC | 310 |

Binding Affinity Determination by SPR

The 2- and 7-series trastuzumab variants had detectable activity at the 20 nM ErbB2 concentrations used. While the 2-series fit quite well to a Langmuir binding model (1:1), the 7-series variants showed complexity in their kinetics as seen by deviations from ideal behaviour in the dissociation phase. This is especially evident with variant 7-5 which shows a complex biphasic off-rate that fit poorly to the Langmuir binding model. The affinity of this variant would likely be lower than the 0.3 nM indicated in Table 5, as the modeled fit uses the slow dissociation phase only. Series 8, those with the heavy chain substitution R59E, did not show any detectable binding activity indicating this position is critical for binding activity of trastuzumab. The wild-type version (2-1) had identical binding behaviour to the commercial trastuzumab.

TABLE 5

Kinetic parameters of ErbB2 - mAb variant binding modeled to a 1:1 binding fit

| | ka 1/Ms | kd 1/s | KD | Chi2 RU |
| --- | --- | --- | --- | --- |
| Variant 7-1 | 7.07E+05 | 1.72E−04 | 2.43E−10 | 3.38 |
| Variant 7-3 | 6.70E+05 | 9.24E−04 | 1.38E−09 | 14.92 |

TABLE 5-continued

Kinetic parameters of ErbB2 - mAb variant binding modeled to a 1:1 binding fit

|  | ka 1/Ms | kd 1/s | KD | Chi2 RU |
|---|---|---|---|---|
| Variant 7-4 | 6.01E+05 | 1.10E−03 | 1.83E−09 | 25.9 |
| Variant 7-5 | 8.12E+05 | 2.11E−04 | 2.59E−10 | 5.48 |
| Variant 7-6 | 5.76E+05 | 2.91E−03 | 5.05E−09 | 3.68 |
| Variant 2-3 | 8.46E+05 | 1.17E−04 | 1.39E−10 | 3.76 |
| Variant 2-4 | 7.47E+05 | 2.95E−04 | 3.95E−10 | 3.55 |
| Variant 2-5 | 7.19E+05 | 1.12E−03 | 1.56E−09 | 11.91 |
| Variant 2-6 | 6.21E+05 | 4.30E−04 | 6.92E−10 | 3.7 |
| Trastuzumab | 8.82E+05 | 2.92E−05 | 3.31E−11 | 5.84 |
| Wild-type 2-1 | 8.56E+05 | 1.66E−05 | 1.94E−11 | 3.99 |

Experimental testing of the designed Trastuzumab mutants using the SPR technique showed that the erbB2 binding affinity is weakened over 100-fold for 1 mutant, between 10-100-fold for 5 mutants, and below 10-fold for another 3 mutants, relative to the parent Trastuzumab antibody (see also FIG. 1).

Evaluation of Antibody Binding to Tumor and Normal Cell Lines

Binding of the antibodies to various cell lines was also determined by indirect flow cytometry as described in the Materials and Methods. As shown in FIG. 3, these results demonstrate weaker binding of 2-5 and 7-6 antibody mutants to HCM cells compared to tumor cells (relative to binding observed for wt control and commercial benchmark). Also as shown in FIG. 4, this result clearly shows that some of the antibody mutants exhibit better binding to tumor relative to normal HEK cells (e.g. 2-5 exhibits 10-12×, 7-6 exhibits 6-8× more binding to tumor than normal). The pattern of binding specificity was similar amongst the tumor cell lines analyzed (SKBr3 or BT474) suggesting that the selectivity of binding is universally high for all tumor cells presenting erbB2 at a density greater than the normal erbB2 density (~3 million receptors per cell or more).

Polynucleotides encoding the various mutant antibody chains are provided below. Substituted codons are italicized and in bold font, and HindIII sites are italicized:

```
Light chain: WT [SEQ ID No. 11]
GGTACCAAGCTTGCCACCATGGTGCTGCAGACCCAGGTGTTCATCTCCCTGCTGCTGTGG

ATCTCTGGCGCCTACGGCGACATCCAGATGACCCAGTCCCCCTCCTCCCTGTCTGCCTCC

GTGGGCGACAGAGTGACCATCACCTGTCGGGCCTCCCAGGATGTGAACACCGCCGTGGCC

TGGTATCAGCAGAAGCCTGGCAAGGCCCCTAAGCTGCTGATCTACTCCGCCTCCTTCCTG

TACTCCGGCGTGCCCTCCCGGTTCTCCGGCTCCAGATCCGGCACCGACTTCACCCTGACC

ATCTCCAGCCTGCAGCCTGAGGACTTCGCCACCTACTACTGCCAGCAGCACTACACCACC

CCTCCAACCTTCGGCCAGGGCACCAAGGTGGAGATCAAGCGGACCGTGGCCGCTCCTTCC

GTGTTCATCTTCCCACCTTCCGACGAGCAGCTGAAGTCCGGCACCGCCTCTGTCGTCTGC

CTGCTGAACAACTTCTACCCTCGGGAGGCCAAGGTGCAGTGGAAGGTGGACAACGCCCTG

CAGTCCGGCAACTCCCAGGAATCCGTCACCGAGCAGGACTCCAAGGACTCTACCTACTCC

CTGTCCTCCACCCTGACCCTGTCCAAGGCCGACTACGAGAAGCACAAGGTGTACGCCTGC

GAAGTGACCCACCAGGGCCTGTCCAGCCCTGTGACCAAGTCCTTCAACCGGGGCGAGTGC

TGATGAAAGCTTGAGCTC

>M1; Light chain: F53N (changed TTC for AAC) [SEQ ID No. 12]
GGTACCAAGCTTGCCACCATGGTGCTGCAGACCCAGGTGTTCATCTCCCTGCTGCTGTGG

ATCTCTGGCGCCTACGGCGACATCCAGATGACCCAGTCCCCCTCCTCCCTGTCTGCCTCC

GTGGGCGACAGAGTGACCATCACCTGTCGGGCCTCCCAGGATGTGAACACCGCCGTGGCC

TGGTATCAGCAGAAGCCTGGCAAGGCCCCTAAGCTGCTGATCTACTCCGCCTCCAAC

CTGTACTCCGGCGTGCCCTCCCGGTTCTCCGGCTCCAGATCCGGCACCGACTTCACCCTG

ACCATCTCCAGCCTGCAGCCTGAGGACTTCGCCACCTACTACTGCCAGCAGCACTACACC

ACCCCTCCAACCTTCGGCCAGGGCACCAAGGTGGAGATCAAGCGGACCGTGGCCGCTCCT

TCCGTGTTCATCTTCCCACCTTCCGACGAGCAGCTGAAGTCCGGCACCGCCTCTGTCGTC

TGCCTGCTGAACAACTTCTACCCTCGGGAGGCCAAGGTGCAGTGGAAGGTGGACAACGCC

CTGCAGTCCGGCAACTCCCAGGAATCCGTCACCGAGCAGGACTCCAAGGACTCTACCTAC

TCCCTGTCCTCCACCCTGACCCTGTCCAAGGCCGACTACGAGAAGCACAAGGTGTACGCC

TGCGAAGTGACCCACCAGGGCCTGTCCAGCCCTGTGACCAAGTCCTTCAACCGGGGCGAG

TGCTGATGAAAGCTTGAGCTC
```

>m2; Light chain: Y92A (changed TAC for GCC) [SEQ ID No. 13]
GGTACCAAGCTTGCCACCATGGTGCTGCAGACCCAGGTGTTCATCTCCCTGCTGCTGTGG

ATCTCTGGCGCCTACGGCGACATCCAGATGACCCAGTCCCCCTCCTCCCTGTCTGCCTCC

GTGGGCGACAGAGTGACCATCACCTGTCGGGCCTCCCAGGATGTGAACACCGCCGTGGCC

TGGTATCAGCAGAAGCCTGGCAAGGCCCCTAAGCTGCTGATCTACTCCGCCTCCTTCCTG

TACTCCGGCGTGCCCTCCCGGTTCTCCGGCTCCAGATCCGGCACCGACTTCACCCTGACC

ATCTCCAGCCTGCAGCCTGAGGACTTCGCCACCTACTACTGCCAGCAGCAC*GCC*ACC

ACCCCTCCAACCTTCGGCCAGGGCACCAAGGTGGAGATCAAGCGGACCGTGGCCGCTCCT

TCCGTGTTCATCTTCCCACCTTCCGACGAGCAGCTGAAGTCCGGCACCGCCTCTGTCGTC

TGCCTGCTGAACAACTTCTACCCTCGGGAGGCCAAGGTGCAGTGGAAGGTGGACAACGCC

CTGCAGTCCGGCAACTCCCAGGAATCCGTCACCGAGCAGGACTCCAAGGACTCTACCTAC

TCCCTGTCCTCCACCCTGACCCTGTCCAAGGCCGACTACGAGAAGCACAAGGTGTACGCC

TGCGAAGTGACCCACCAGGGCCTGTCCAGCCCTGTGACCAAGTCCTTCAACCGGGGCGAG

TGCTGATGAAAGCTTGAGCTC

>m3; Light chain: F53N,Y92A (changed TTC for AAC and TAC for GCC) [SEQ ID No. 14]
GGTACCAAGCTTGCCACCATGGTGCTGCAGACCCAGGTGTTCATCTCCCTGCTGCTGTGG

ATCTCTGGCGCCTACGGCGACATCCAGATGACCCAGTCCCCCTCCTCCCTGTCTGCCTCC

GTGGGCGACAGAGTGACCATCACCTGTCGGGCCTCCCAGGATGTGAACACCGCCGTGGCC

TGGTATCAGCAGAAGCCTGGCAAGGCCCCTAAGCTGCTGATCTACTCCGCCTC*AAC*

CTGTACTCCGGCGTGCCCTCCCGGTTCTCCGGCTCCAGATCCGGCACCGACTTCACCCTG

ACCATCTCCAGCCTGCAGCCTGAGGACTTCGCCACCTACTACTGCCAGCAGCAC*GCC*

ACCACCCCTCCAACCTTCGGCCAGGGCACCAAGGTGGAGATCAAGCGGACCGTGGCCGCT

CCTTCCGTGTTCATCTTCCCACCTTCCGACGAGCAGCTGAAGTCCGGCACCGCCTCTGTC

GTCTGCCTGCTGAACAACTTCTACCCTCGGGAGGCCAAGGTGCAGTGGAAGGTGGACAAC

GCCCTGCAGTCCGGCAACTCCCAGGAATCCGTCACCGAGCAGGACTCCAAGGACTCTACC

TACTCCCTGTCCTCCACCCTGACCCTGTCCAAGGCCGACTACGAGAAGCACAAGGTGTAC

GCCTGCGAAGTGACCCACCAGGGCCTGTCCAGCCCTGTGACCAAGTCCTTCAACCGGGGC

GAGTGCTGATGAAAGCTTGAGCTC

>m4; Light chain: N30D (changed AAC for GAC) [SEQ ID No. 15]
GGTACCAAGCTTGCCACCATGGTGCTGCAGACCCAGGTGTTCATCTCCCTGCTGCTGTGG

ATCTCTGGCGCCTACGGCGACATCCAGATGACCCAGTCCCCCTCCTCCCTGTCTGCCTCC

GTGGGCGACAGAGTGACCATCACCTGTCGGGCCTCCCAGGATGTG*GAC*ACCGCCGTG

GCCTGGTATCAGCAGAAGCCTGGCAAGGCCCCTAAGCTGCTGATCTACTCCGCCTCCTTC

CTGTACTCCGGCGTGCCCTCCCGGTTCTCCGGCTCCAGATCCGGCACCGACTTCACCCTG

ACCATCTCCAGCCTGCAGCCTGAGGACTTCGCCACCTACTACTGCCAGCAGCACTACACC

ACCCCTCCAACCTTCGGCCAGGGCACCAAGGTGGAGATCAAGCGGACCGTGGCCGCTCCT

TCCGTGTTCATCTTCCCACCTTCCGACGAGCAGCTGAAGTCCGGCACCGCCTCTGTCGTC

TGCCTGCTGAACAACTTCTACCCTCGGGAGGCCAAGGTGCAGTGGAAGGTGGACAACGCC

CTGCAGTCCGGCAACTCCCAGGAATCCGTCACCGAGCAGGACTCCAAGGACTCTACCTAC

TCCCTGTCCTCCACCCTGACCCTGTCCAAGGCCGACTACGAGAAGCACAAGGTGTACGCC

-continued

TGCGAAGTGACCCACCAGGGCCTGTCCAGCCCTGTGACCAAGTCCTTCAACCGGGGCGAG

TGCTGATGAAAGCTTGAGCTC

Heavy chain: wT [SEQ ID No. 16]
TTAATTAAGCTTGCCACCATGGACTGGACCTGGCGGATCCTGTTTCTGGTGGCCGCTGCT

ACCGGCACACACGCCGAGGTGCAGCTGGTGGAGTCTGGCGGAGGACTGGTGCAGCCTGGC

GGCTCCCTGAGACTGTCTTGCGCCGCCTCCGGCTTCAACATCAAGGACACCTACATCCAC

TGGGTCCGGCAGGCTCCAGGCAAGGGACTGGAATGGGTGGCCCGGATCTACCCTACCAAC

GGCTACACCAGATACGCCGACTCCGTGAAGGGCCGGTTCACCATCTCCGCCGACACCTCC

AAGAACACCGCCTACCTGCAGATGAACTCCCTGAGGGCCGAGGACACCGCCGTGTACTAC

TGCTCCAGATGGGGAGGCGACGGCTTCTACGCCATGGACTACTGGGGCCAGGGCACCCTG

GTCACTGTGTCCTCTGCCTCCACCAAGGGCCCTTCCGTGTTCCCTCTGGCCCCTTCCAGC

AAGTCTACCTCTGGCGGCACCGCTGCTCTGGGCTGCCTGGTCAAGGACTACTTCCCTGAG

CCTGTGACCGTGTCCTGGAACTCTGGCGCCCTGACCTCCGGCGTGCACACCTTCCCTGCC

GTGCTGCAGTCCTCCGGCCTGTACTCCCTGTCCTCCGTCGTGACCGTGCCTTCCTCTAGC

CTGGGCACCCAGACCTACATCTGCAACGTGAACCACAAGCCTTCCAACACCAAGGTGGAC

AAGAAGGTGGAGCCTAAGTCCTGCGACAAGACCCACACCTGTCCTCCATGCCCTGCCCCT

GAGCTGCTGGGCGGACCCTCCGTGTTCCTGTTCCCTCCAAAGCCTAAGGACACCCTGATG

ATCTCCCGGACCCCTGAAGTGACCTGCGTGGTGGTGGACGTGTCCCACGAGGATCCTGAA

GTGAAGTTCAATTGGTACGTGGACGGCGTGGAGGTGCACAACGCCAAGACCAAGCCTCGG

GAGGAACAGTACAACTCCACCTACCGGGTGGTGTCCGTGCTGACCCTGCTGCACCAGGAC

TGGCTGAACGGCAAAGAGTATAAGTGCAAAGTCTCCAACAAGGCCCTGCCTGCCCCTATC

GAAAAGACCATCTCCAAGGCCAAGGGCCAGCCTCGGGAACCTCAGGTGTACACCCTGCCT

CCCAGCAGGGACGAGCTGACCAAGAACCAGGTGTCCCTGACCTGTCTGGTCAAGGGCTTC

TACCCTTCCGATATCGCCGTGGAGTGGGAGTCTAACGGCCAGCCTGAGAACAACTACAAG

ACCACCCCTCCTGTGCTGGACTCCGACGGCTCCTTCTTCCTGTACTCCAAACTGACCGTG

GACAAGTCCCGGTGGCAGCAGGGCAACGTGTTCTCCTGCTCCGTGATGCACGAGGCCCTG

CACAACCACTACACCCAGAAGTCCCTGTCCCTGTCTCCTGGCAAGTGATGAAAGCTTGGC

GCGCC

>m5; Heavy chain: Y57A (Changed TAC for GCC) [SEQ ID No. 17]
TTAATTAAGCTTGCCACCATGGACTGGACCTGGCGGATCCTGTTTCTGGTGGCCGCTGCT

ACCGGCACACACGCCGAGGTGCAGCTGGTGGAGTCTGGCGGAGGACTGGTGCAGCCTGGC

CGCTCCCTGAGACTGTCTTGCGCCGCCTCCGGCTTCAACATCAAGGACACCTACATCCAC

TGGGTCCGGCAGGCTCCAGGCAAGGGACTGGAATGGGTGGCCCGGATCTACCCTACCAAC

GGC*GCC*ACCAGATACGCCGACTCCGTGAAGGGCCGGTTCACCATCTCCGCCGACACCT

CCAAGAACACCGCCTACCTGCAGATGAACTCCCTGAGGGCCGAGGACACCGCCGTGTACT

ACTGCTCCAGATGGGGAGGCGACGGCTTCTACGCCATGGACTACTGGGGCCAGGGCACCC

TGGTCACTGTGTCCTCTGCCTCCACCAAGGGCCCTTCCGTGTTCCCTCTGGCCCCTTCCA

GCAAGTCTACCTCTGGCGGCACCGCTGCTCTGGGCTGCCTGGTCAAGGACTACTTCCCTG

AGCCTGTGACCGTGTCCTGGAACTCTGGCGCCCTGACCTCCGGCGTGCACACCTTCCCTG

CCGTGCTGCAGTCCTCCGGCCTGTACTCCCTGTCCTCCGTCGTGACCGTGCCTTCCTCTA

GCCTGGGCACCCAGACCTACATCTGCAACGTGAACCACAAGCCTTCCAACACCAAGGTGG

ACAAGAAGGTGGAGCCTAAGTCCTGCGACAAGACCCACACCTGTCCTCCATGCCCTGCCC

CTGAGCTGCTGGGCGGACCCTCCGTGTTCCTGTTCCCTCCAAAGCCTAAGGACACCCTGA

TGATCTCCCGGACCCCTGAAGTGACCTGCGTGGTGGTGGACGTGTCCCACGAGGATCCTG

AAGTGAAGTTCAATTGGTACGTGGACGGCGTGGAGGTGCACAACGCCAAGACCAAGCCTC

GGGAGGAACAGTACAACTCCACCTACCGGGTGGTGTCCGTGCTGACCGTGCTGCACCAGG

ACTGGCTGAACGGCAAAGAGTATAAGTGCAAAGTCTCCAACAAGGCCCTGCCTGCCCCTA

TCGAAAAGACCATCTCCAAGGCCAAGGGCCAGCCTCGGGAACCTCAGGTGTACACCCTGC

CTCCCAGCAGGGACGAGCTGACCAAGAACCAGGTGTCCCTGACCTGTCTGGTCAAGGGCT

TCTACCCTTCCGATATCGCCGTGGAGTGGGAGTCTAACGGCCAGCCTGAGAACAACTACA

AGACCACCCCTCCTGTGCTGGACTCCGACGGCTCCTTCTTCCTGTACTCCAAACTGACCG

TGGACAAGTCCCGGTGGCAGCAGGGCAACGTGTTCTCCTGCTCCGTGATGCACGAGGCCC

TGCACAACCACTACACCCAGAAGTCCCTGTCCCTGTCTCCTGGCAAGTGATGAAAGCTTG

GCGCGCC

>m6; Heavy chain: R59E (changed AGA for GAG) [SEQ ID No. 18]
TTAATTAAGCTTGCCACCATGCACTGGACCTGGCGGATCCTGTTTCTGGTGGCCGCTGCT

ACCGGCACACACGCCGAGGTGCAGCTGGTGGAGTCTGGCGGAGGACTGGTGCAGCCTGGC

GGCTCCCTGAGACTGTCTTGCGCCGCCTCCGGCTTCAACATCAAGGACACCTACATCCAC

TGGGTCCGGCAGGCTCCAGGCAAGGGACTGGAATGGGTGGCCCGGATCTACCCTACCAAC

GGCTACACCGAGTACGCCGACTCCGTGAAGGGCCGGTTCACCATCTCCGCCGACACCT

CCAAGAACACCGCCTACCTGCAGATGAACTCCCTGAGGGCCGAGGACACCGCCGTGTACT

ACTGCTCCAGATGGGGAGGCGACGGCTTCTACGCCATGGACTACTGGGGCCAGGGCACCC

TGGTCACTGTGTCCTCTGCCTCCACCAAGGGCCCTTCCGTGTTCCCTCTGGCCCCTTCCA

GCAAGTCTACCTCTGGCGGCACCGCTGCTCTGGGCTGCCTGGTCAAGGACTACTTCCCTG

AGCCTGTGACCGTGTCCTGGAACTCTGGCGCCCTGACCTCCGGCGTGCACACCTTCCCTG

CCGTGCTGCAGTCCTCCGGCCTGTACTCCCTGTCCTCCGTCGTGACCGTGCCCTTCCTCTA

GCCTGGGCACCCAGACCTACATCTGCAACGTGAACCACAAGCCTTCCAACACCAAGGTGG

ACAAGAAGGTGGAGCCTAAGTCCTGCGACAAGACCCACACCTGTCCTCCATGCCCTGCCC

CTGAGCTGCTGGGCGGACCCTCCGTGTTCCTGTTCCCTCCAAAGCCTAAGGACACCCTGA

TGATCTCCCGGACCCCTGAAGTGACCTGCGTGGTGGTGGACGTGTCCCACGAGGATCCTG

AAGTGAAGTTCAATTGGTACGTGGACGGCGTGGAGGTGCACAACGCCAAGACCAAGCCTC

GGGAGGAACAGTACAACTCCACCTACCGGGTGGTGTCCGTGCTGACCGTGCTGCACCAGG

ACTGGCTGAACGGCAAAGAGTATAAGTGCAAAGTCTCCAACAAGGCCCTGCCTGCCCCTA

TCGAAAAGACCATCTCCAAGGCCAAGGGCCAGCCTCGGGAACCTCAGGTGTACACCCTGC

CTCCCAGCAGGGACGAGCTGACCAAGAACCAGGTGTCCCTGACCTGTCTGGTCAAGGGCT

TCTACCCTTCCGATATCGCCGTGGAGTGGGAGTCTAACGGCCAGCCTGAGAACAACTACA

AGACCACCCCTCCTGTGCTGGACTCCGACGGCTCCTTCTTCCTGTACTCCAAACTGACCG

TGGACAAGTCCCGGTGGCAGCAGGGCAACGTGTTCTCCTGCTCCGTGATGCACGAGGCCC

TGCACAACCACTACACCCAGAAGTCCCTGTCCCTGTCTCCTGGCAAGTGATGAAAGCTTG

GCGCGCC

Amino acid sequences constituting the antibody mutant chains are provided below. The signal peptide is indicated using lower case letters and is not included in the residue numbering. Mutated positions are italicized and in bold font.

```
Anti-HER2 Light chain wild-type [SEQ ID No. 19]
mvlqtqvfislllwisgaygDIQMTQSPSSLSASVGDRVTITCRASQDVNTAVAWYQQKP

GKAPKLLIYSASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC

Anti-HER2 Heavy chain wild-type [SEQ ID No. 20]
.........|.........|.........|.........|.........|.........|
mdwtwrilflvaaatgthaEVQLVESGGGLVQPGGSLRLSCAASGFNIKDTYIHWVRQAP

GKGLEWVARIYPTNGYTRYADSVKGRFTISADTSENTAYLQMNSLRAEDTAVYYCSRWGG

DGFYAMDYWGQGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSNTKVDKKVEPK

SCDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISK

AKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

Mutant sequences
>m1; Light chain: F53N [SEQ ID No. 21]
mvlqtqvfislllwisgaygDIQMTQSPSSLSASVGDRVTITCRASQDVNTAVAWYQQKP

GKAPKLLIYSASN LYSGVPSRFSGSRSGTDFTLTISSLQPEDFATYYCQQHYTTPPT

FGQGTKVEIKRTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKSFNRGEC

>m2; Light chain: Y92A [SEQ ID No. 22]
mvlqtqvfislllwisgaygDIQMTQSPSSLSASVGDRVTITCRASQDVNTAVAWYQQKP

GKAPKLLIYSASFLYSGVPSRFSGSRSGTDFTLTISSLQPEDFATYYCQQHA TTPPT

EGQGTKVEIKRTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKSFNRGEC

>m3; Light chain: F53N,Y92A [SEQ ID No. 23]
mvlqtqvfislllwisgaygDIQMTQSPSSLSASVGDRVTITCRASQDVNTAVAWYQQKP

*GKAPKLLIYSASN LYSGVPSRFSGSRSGTDFTLTISSLQPEDFATYYCQQHA TTPPT*

*FGQGTKVEIKRTVAAPSVFIFPPSDEQLKSGTASVVCLLNNFYPREAKVQWKVDNALQSG*

NSQESVTEQDSKDSTYSLSSTLTLSKADYEKHKVYACEVTHQGLSSPVTKSFNRGEC

>m4; Light chain: N30D [SEQ ID No. 24]
mvlqtqvfislllwisgaygDIQMTQSPSSLSASVGDRVTITCRASQDVD TAVAWYQ

QKPGKAPKLLIYSASFLYSGVPSRFSGSRSGTDFTLTISSLQPEDFATYYCQQHYTTPPT

EGQGTKVEIKRTVAAPSVFIFPPSDEQLKSGTASVVCLLNNEYPREAKVQWKVDNALQSG

NSQESVTEQDSKDSTYSLSSTLTLSKADYEKHKVYACEVTHQGLSSPVTKSFNRGEC

>m5; Heavy chain: Y57A [SEQ ID No. 25]
mdwtwrilflvaaatgthaEVQLVESGGGLVQPGGSLRLSCAASGFNIKDTYIHWVRQAP

GKGLEWVARTYPTNGA TRYADSVKGRFTISADTSKNTAYLQMNSLRAEDTAVYYCSR

WGGDGFYAMDYWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKKV

EPKSCDKTHTCPPCPAPELLGGPSVFLFPRKPKDTLMISRTPEVTCVVVDVSHEDPEVKF
```

NWYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

>m6; Heavy chain: R59E [SEQ ID No. 26]
mdwtwrilflvaaatgthaEVQLVESGGGLVQPGGSLRLSCAASGENIKDTYIHWVRQAP

GKGLEWVARTYPTNGYTE YADSVKGRFTISADTSKNTAYLQMNSLRAEDTAVYYCSR

WGGDGFYAMDYWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVVDVSHEDPEVKF

NWYVDGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLSPGK

REFERENCES

TS1. Cho, H. S., Mason, K., Ramyar, K. X., Stanley, A. M., Gabelli, S. B., Denney, D. W., and Leahy, D. J. (2003) Structure of the extracellular region of HER2 alone and in complex with the Herceptin Fab, Nature 421, 756-760.

TS2. Li, Z. and Scheraga, H. A. (1987) Monte Carlo-minimization approach to the multiple-minima problem in protein folding, Proc. Nat. Acad. Sci. U.S.A. 84, 6611-6615.

TS3. Naim, M., Bhat, S., Rankin, K. N., Dennis, S., Chowdhury, S. F., Siddiqi, I., Drabik, P., Sulea, T., Bayl), C. I., Jakalian, A., and Purisima, E. O. (2007) Solvated Interaction Energy (SIE) for Scoring Protein-Ligand Binding Affinities. 1. Exploring the Parameter Space, J. Chem. Inf. Model. 47, 122-133.

TS4. Selzer, T., Albeck, S., and Schreiber, G. (2000) Rational design of faster associating and tighter binding protein complexes, Nat. Struct. Mol. Biol. 7, 537-541.

SEQUENCE LISTING

```
<160> NUMBER OF SEQ ID NOS: 26

<210> SEQ ID NO 1
<211> LENGTH: 10
<212> TYPE: PRT
<213> ORGANISM: Artificial Sequence
<220> FEATURE:
<223> OTHER INFORMATION: Heavy chain CDR1

<400> SEQUENCE: 1

Gly Phe Asn Ile Lys Asp Thr Tyr Ile His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Heavy chain CDR2
<220> FEATURE:
<221> NAME/KEY: MISC_FEATURE
<222> LOCATION: (8)..(8)
<223> OTHER INFORMATION: Xaa is Tyr or an amino acid having a side chain
      that is nonpolar and/or a side chain that is non-neutral and/or a
      side chain that is not large
<220> FEATURE:
<221> NAME/KEY: MISC_FEATURE
<222> LOCATION: (10)..(10)
<223> OTHER INFORMATION: Xaa is Arg or an amino acid having a side chain
      that is nonpolar and/or a side chain that is non-neutral and/or a
      side chain that is not large

<400> SEQUENCE: 2

Arg Ile Tyr Pro Thr Asn Gly Xaa Thr Xaa Tyr Ala Asp Ser Val Lys
1               5                   10                  15

Gly
```

<210> SEQ ID NO 3
<211> LENGTH: 11
<212> TYPE: PRT
<213> ORGANISM: Artificial Sequence
<220> FEATURE:
<223> OTHER INFORMATION: Heavy chain CDR3

<400> SEQUENCE: 3

Trp Gly Gly Asp Gly Phe Tyr Ala Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Light chain CDR1
<220> FEATURE:
<221> NAME/KEY: MISC_FEATURE
<222> LOCATION: (7)..(7)
<223> OTHER INFORMATION: Xaa is Asn or an amino acid having a side chain
      that is either nonpolar and/or is negative or positive in charge
      and/or may not be small

<400> SEQUENCE: 4

Arg Ala Ser Gln Asp Val Xaa Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Light chain CDR2
<220> FEATURE:
<221> NAME/KEY: MISC_FEATURE
<222> LOCATION: (4)..(4)
<223> OTHER INFORMATION: Xaa is Phe or an amino acid having a side chain
      that is either polar and/or is charge positive or negative and/or
      is not large

<400> SEQUENCE: 5

Ser Ala Ser Xaa Leu Tyr Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Light chain CDR3
<220> FEATURE:
<221> NAME/KEY: MISC_FEATURE
<222> LOCATION: (4)..(4)
<223> OTHER INFORMATION: Xaa is Tyr or an amino acid having a side chain
      that is nonpolar and/or a side chain that is non-neutral and/or is
      not large.

<400> SEQUENCE: 6

Gln Gln His Xaa Thr Thr Pro Pro Thr
1               5

<210> SEQ ID NO 7
<211> LENGTH: 107
<212> TYPE: PRT
<213> ORGANISM: Artificial Sequence
<220> FEATURE:
<223> OTHER INFORMATION: Light chain variable region
<220> FEATURE:

-continued

```
<221> NAME/KEY: MISC_FEATURE
<222> LOCATION: (30)..(30)
<223> OTHER INFORMATION: Xaa is Asn or an amino acid having a side chain
      that is either nonpolar and/or is negative or positive in charge
      and/or may not be small.
<220> FEATURE:
<221> NAME/KEY: MISC_FEATURE
<222> LOCATION: (53)..(53)
<223> OTHER INFORMATION: Xaa is Phe or an amino acid having a side chain
      that is either polar and/or is charge positive or negative and/or
      is not large.
<220> FEATURE:
<221> NAME/KEY: MISC_FEATURE
<222> LOCATION: (92)..(92)
<223> OTHER INFORMATION: Xaa is Tyr or an amino acid having a side chain
      that is nonpolar and/or a side chain that is non-neutral and/or is
      not large.

<400> SEQUENCE: 7

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Xaa Thr Ala
             20                  25                  30

Val Ala Trp Tyr Gln Gln Lys Pro Gly Lys Ala Pro Lys Leu Leu Ile
         35                  40                  45

Tyr Ser Ala Ser Xaa Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Xaa Thr Thr Pro Pro
                 85                  90                  95

Thr Phe Gly Gln Gly Thr Lys Val Glu Ile Lys
            100                 105

<210> SEQ ID NO 8
<211> LENGTH: 120
<212> TYPE: PRT
<213> ORGANISM: Artificial Sequence
<220> FEATURE:
<223> OTHER INFORMATION: Heavy chain variable region
<220> FEATURE:
<221> NAME/KEY: MISC_FEATURE
<222> LOCATION: (57)..(57)
<223> OTHER INFORMATION: Xaa is Tyr or an amino acid having a side chain
      that is nonpolar and/or a side chain that is non-neutral and/or a
      side chain that is not large.
<220> FEATURE:
<221> NAME/KEY: MISC_FEATURE
<222> LOCATION: (59)..(59)
<223> OTHER INFORMATION: Xaa is Arg or an amino acid having a side chain
      that is nonpolar and/or is charge neutral or negative and/or is
      not large.

<400> SEQUENCE: 8

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Xaa Thr Xaa Tyr Ala Asp Ser Val
     50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95
Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 9
<211> LENGTH: 214
<212> TYPE: PRT
<213> ORGANISM: Artificial Sequence
<220> FEATURE:
<223> OTHER INFORMATION: Light chain
<220> FEATURE:
<221> NAME/KEY: MISC_FEATURE
<222> LOCATION: (30)..(30)
<223> OTHER INFORMATION: Xaa is Asn or an amino acid having a side chain
      that is either nonpolar and/or is negative or positive in charge
      and/or may not be small.
<220> FEATURE:
<221> NAME/KEY: MISC_FEATURE
<222> LOCATION: (53)..(53)
<223> OTHER INFORMATION: Xaa is Phe or an amino acid having a side chain
      that is either polar and/or is charge positive or negative and/or
      is not large.
<220> FEATURE:
<221> NAME/KEY: MISC_FEATURE
<222> LOCATION: (92)..(92)
<223> OTHER INFORMATION: Xaa is Tyr or an amino acid having a side chain
      that is either nonpolar and/or a side chain that is non-neutral
      and/or is not large.

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Xaa Thr Ala
            20                  25                  30

Val Ala Trp Tyr Gln Gln Lys Pro Gly Lys Ala Pro Lys Leu Leu Ile
        35                  40                  45

Tyr Ser Ala Ser Xaa Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Xaa Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 10
<211> LENGTH: 450
<212> TYPE: PRT
<213> ORGANISM: Artificial Sequence
<220> FEATURE:
<223> OTHER INFORMATION: Heavy chain
<220> FEATURE:
<221> NAME/KEY: MISC_FEATURE
<222> LOCATION: (57)..(57)
<223> OTHER INFORMATION: Xaa is Tyr or an amino acid having a side chain
      that is nonpolar and/or a side chain that is non-neutral and/or a
      side chain that is not large.
<220> FEATURE:
<221> NAME/KEY: MISC_FEATURE
<222> LOCATION: (59)..(59)
<223> OTHER INFORMATION: Xaa is Arg or an amino acid having a side chain
      that is nonpolar and/or is charge neutral or negative and/or is
      not large.

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Xaa Thr Xaa Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Thr Pro Pro Cys Pro Arg Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
```

```
                305                 310                 315                 320
Glu Tyr Lys Cys Lys Val Ser Asn Lys Ala Leu Pro Ala Pro Ile Glu
                    325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                    405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
            435                 440                 445
Gly Lys
    450

<210> SEQ ID NO 11
<211> LENGTH: 738
<212> TYPE: DNA
<213> ORGANISM: Artificial Sequence
<220> FEATURE:
<223> OTHER INFORMATION: Light chain

<400> SEQUENCE: 11
ggtaccaagc ttgccaccat ggtgctgcag acccaggtgt tcatctccct gctgctgtgg      60
atctctggcg cctacggcga catccagatg acccagtccc cctcctccct gtctgcctcc     120
gtgggcgaca gagtgaccat cacctgtcgg gcctcccagg atgtgaacac cgccgtggcc     180
tggtatcagc agaagcctgg caaggcccct aagctgctga tctactccgc ctccttcctg     240
tactccggcg tgccctcccg gttctccggc tccagatccg gcaccgactt caccctgacc     300
atctccagcc tgcagcctga ggacttcgcc acctactact gccagcagca ctacaccacc     360
cctccaacct tcggccaggg caccaaggtg gagatcaagc ggaccgtggc cgctccttcc     420
gtgttcatct tcccaccttc cgacgagcag ctgaagtccg gcaccgcctc tgtcgtctgc     480
ctgctgaaca acttctaccc tcgggaggcc aaggtgcagt ggaaggtgga caacgccctg     540
cagtccggca actcccagga atccgtcacc gagcaggact ccaaggactc tacctactcc     600
ctgtcctcca ccctgacect gtccaaggcc gactacgaga agcacaaggt gtacgcctgc     660
gaagtgaccc accagggcct gtccagccct gtgaccaagt ccttcaaccg gggcgagtgc     720
tgatgaaagc ttgagctc                                                  738

<210> SEQ ID NO 12
<211> LENGTH: 738
<212> TYPE: DNA
<213> ORGANISM: Artificial Sequence
<220> FEATURE:
<223> OTHER INFORMATION: Light chain F53N

<400> SEQUENCE: 12
ggtaccaagc ttgccaccat ggtgctgcag acccaggtgt tcatctccct gctgctgtgg      60
atctctggcg cctacggcga catccagatg acccagtccc cctcctccct gtctgcctcc     120
```

```
gtgggcgaca gagtgaccat cacctgtcgg gcctcccagg atgtgaacac cgccgtggcc    180
tggtatcagc agaagcctgg caaggcccct aagctgctga tctactccgc ctccaacctg    240
tactccggcg tgccctcccg gttctccggc tccagatccg gcaccgactt caccctgacc    300
atctccagcc tgcagcctga ggacttcgcc acctactact gccagcagca ctacaccacc    360
cctccaacct tcggccaggg caccaaggtg gagatcaagc ggaccgtggc cgctccttcc    420
gtgttcatct tcccaccttc cgacgagcag ctgaagtccg gcaccgcctc tgtcgtctgc    480
ctgctgaaca acttctaccc tcgggaggcc aaggtgcagt ggaaggtgga caacgccctg    540
cagtccggca actcccagga atccgtcacc gagcaggact ccaaggactc tacctactcc    600
ctgtcctcca ccctgaccct gtccaaggcc gactacgaga agcacaaggt gtacgcctgc    660
gaagtgaccc caggggcct gtccagccct gtgaccaagt ccttcaaccg gggcgagtgc    720
tgatgaaagc ttgagctc                                                  738

<210> SEQ ID NO 13
<211> LENGTH: 738
<212> TYPE: DNA
<213> ORGANISM: Artificial Sequence
<220> FEATURE:
<223> OTHER INFORMATION: Light chain Y92A

<400> SEQUENCE: 13
ggtaccaagc ttgccaccat ggtgctgcag acccaggtgt tcatctccct gctgctgtgg     60
atctctggcg cctacggcga catccagatg acccagtccc cctcctccct gtctgcctcc    120
gtgggcgaca gagtgaccat cacctgtcgg gcctcccagg atgtgaacac cgccgtggcc    180
tggtatcagc agaagcctgg caaggcccct aagctgctga tctactccgc ctccttcctg    240
tactccggcg tgccctcccg gttctccggc tccagatccg gcaccgactt caccctgacc    300
atctccagcc tgcagcctga ggacttcgcc acctactact gccagcagca cgccaccacc    360
cctccaacct tcggccaggg caccaaggtg gagatcaagc ggaccgtggc cgctccttcc    420
gtgttcatct tcccaccttc cgacgagcag ctgaagtccg gcaccgcctc tgtcgtctgc    480
ctgctgaaca acttctaccc tcgggaggcc aaggtgcagt ggaaggtgga caacgccctg    540
cagtccggca actcccagga atccgtcacc gagcaggact ccaaggactc tacctactcc    600
ctgtcctcca ccctgaccct gtccaaggcc gactacgaga agcacaaggt gtacgcctgc    660
gaagtgaccc caggggcct gtccagccct gtgaccaagt ccttcaaccg gggcgagtgc    720
tgatgaaagc ttgagctc                                                  738

<210> SEQ ID NO 14
<211> LENGTH: 738
<212> TYPE: DNA
<213> ORGANISM: Artificial Sequence
<220> FEATURE:
<223> OTHER INFORMATION: Light chain, F53N, Y92A

<400> SEQUENCE: 14
ggtaccaagc ttgccaccat ggtgctgcag acccaggtgt tcatctccct gctgctgtgg     60
atctctggcg cctacggcga catccagatg acccagtccc cctcctccct gtctgcctcc    120
gtgggcgaca gagtgaccat cacctgtcgg gcctcccagg atgtgaacac cgccgtggcc    180
tggtatcagc agaagcctgg caaggcccct aagctgctga tctactccgc ctccaacctg    240
tactccggcg tgccctcccg gttctccggc tccagatccg gcaccgactt caccctgacc    300
atctccagcc tgcagcctga ggacttcgcc acctactact gccagcagca cgccaccacc    360
```

```
cctccaacct tcggccaggg caccaaggtg gagatcaagc ggaccgtggc cgctccttcc    420
gtgttcatct tcccaccttc cgacgagcag ctgaagtccg gcaccgcctc tgtcgtctgc    480
ctgctgaaca acttctaccc tcgggaggcc aaggtgcagt ggaaggtgga caacgccctg    540
cagtccggca actcccagga atccgtcacc gagcaggact ccaaggactc tacctactcc    600
ctgtcctcca ccctgaccct gtccaaggcc gactacgaga agcacaaggt gtacgcctgc    660
gaagtgaccc caccagggcct gtccagccct gtgaccaagt ccttcaaccg gggcgagtgc    720
tgatgaaagc ttgagctc                                                  738
```

```
<210> SEQ ID NO 15
<211> LENGTH: 738
<212> TYPE: DNA
<213> ORGANISM: Artificial Sequence
<220> FEATURE:
<223> OTHER INFORMATION: Light chain N30D

<400> SEQUENCE: 15
ggtaccaagc ttgccaccat ggtgctgcag acccaggtgt tcatctccct gctgctgtgg    60
atctctggcg cctacggcga catccagatg acccagtccc cctcctccct gtctgcctcc    120
gtgggcgaca gagtgaccat cacctgtcgg gcctcccagg atgtggacac cgccgtggcc    180
tggtatcagc agaagcctgg caaggcccct aagctgctga tctactccgc ctccttcctg    240
tactccggcg tgccctcccg gttctccggc tccagatccg gcaccgactt caccctgacc    300
atctccagcc tgcagcctga ggacttcgcc acctactact gccagcagca ctacaccacc    360
cctccaacct tcggccaggg caccaaggtg gagatcaagc ggaccgtggc cgctccttcc    420
gtgttcatct tcccaccttc cgacgagcag ctgaagtccg gcaccgcctc tgtcgtctgc    480
ctgctgaaca acttctaccc tcgggaggcc aaggtgcagt ggaaggtgga caacgccctg    540
cagtccggca actcccagga atccgtcacc gagcaggact ccaaggactc tacctactcc    600
ctgtcctcca ccctgaccct gtccaaggcc gactacgaga agcacaaggt gtacgcctgc    660
gaagtgaccc caccagggcct gtccagccct gtgaccaagt ccttcaaccg gggcgagtgc    720
tgatgaaagc ttgagctc                                                  738
```

```
<210> SEQ ID NO 16
<211> LENGTH: 1445
<212> TYPE: DNA
<213> ORGANISM: Artificial Sequence
<220> FEATURE:
<223> OTHER INFORMATION: Heavy chain

<400> SEQUENCE: 16
ttaattaagc ttgccaccat ggactggacc tggcggatcc tgtttctggt ggccgctgct    60
accggcacac acgccgaggt gcagctggtg gagtctggcg gaggactggt gcagcctggc    120
ggctccctga ctgtctgttg cgccgcctcc ggcttcaaca tcaaggacac ctacatccac    180
tgggtccggc aggctccagg caagggactg gaatgggtgg cccggatcta ccctaccaac    240
ggctacacca gatacgccga ctccgtgaag ggccggttca ccatctcccg cgacacctcc    300
aagaacaccg cctacctgca gatgaactcc ctgagggccg aggacaccgc cgtgtactac    360
tgctccagat ggggaggcga cggcttctac gccatggact actggggcca gggcaccctg    420
gtcactgtgt cctctgcctc caccaagggc ccttccgtgt tcctctggc ccttccagc    480 aagtctacct ctggcggcac cgctgctctg ggctgcctgg tcaaggacta cttccctgag    540
```

```
cctgtgaccg tgtcctggaa ctctggcgcc ctgacctccg gcgtgcacac cttccctgcc    600
gtgctgcagt cctccggcct gtactccctg tcctccgtcg tgaccgtgcc ttcctctagc    660
ctgggcaccc agacctacat ctgcaacgtg aaccacaagc cttccaacac caaggtggac    720
aagaaggtgg agcctaagtc ctgcgacaag acccacacct gtcctccatg ccctgcccct    780
gagctgctgg gcggacccte cgtgttcctg ttccctccaa agcctaagga caccctgatg    840
atctcccgga cccctgaagt gacctgcgtg gtggtggacg tgtcccacga ggatcctgaa    900
gtgaagttca attggtacgt ggacggcgtg gaggtgcaca cgccaagac caagcctcgg    960 gaggaacagt acaactccac ctaccgggtg gtgtccgtgc tgaccgtgct gcaccaggac    1020
tggctgaacg gcaaagagta taagtgcaaa gtctccaaca aggccctgcc tgcccctatc    1080
gaaaagacca tctccaaggc caagggccag cctcgggaac ctcaggtgta caccctgcct    1140
cccagcaggg acgagctgac caagaaccag gtgtccctga cctgtctggt caagggcttc    1200
taccctcccg atatcgccgt ggagtgggag tctaacggcc agcctgagaa caactacaag    1260 accaccccctc ctgtgctgga ctccgacggc tccttcttcc tgtactccaa actgaccgtg    1320
gacaagtccc ggtggcagca gggcaacgtg ttctcctgct ccgtgatgca cgaggccctg    1380
cacaaccact acacccagaa gtccctgtcc ctgtctcctg caagtgatg aaagcttggc    1440 gcgcc                                                                1445

<210> SEQ ID NO 17
<211> LENGTH: 1445
<212> TYPE: DNA
<213> ORGANISM: Artificial Sequence
<220> FEATURE:
<223> OTHER INFORMATION: Heavy chain Y57A

<400> SEQUENCE: 17
ttaattaagc ttgccaccat ggactggacc tggcggatcc tgtttctggt ggccgctgct     60
accggcacac acgccgaggt gcagctggtg gagtctggcg gaggactggt gcagcctggc    120
ggctccctga actgtcttg cgccgcctcc ggcttcaaca tcaaggacac ctacatccac    180
tgggtccggc aggctccagg caagggactg gaatgggtgg cccggatcta ccctaccaac    240
ggcgccacca gatacgccga ctccgtgaag ggccggttca ccatctccgc cgacacctcc    300
aagaacaccg cctacctgca gatgaactcc ctgagggccg aggacaccgc cgtgtactac    360
tgctccagat ggggaggcga cggcttctac gccatggact actggggcca gggcaccctg    420
gtcactgtgt cctctgcctc caccaagggc ccttccgtgt tccctctggc cccttccagc    480
aagtctacct ctggcggcac cgctgctctg ggctgcctgg tcaaggacta cttccctgag    540
cctgtgaccg tgtcctggaa ctctggcgcc ctgacctccg gcgtgcacac cttccctgcc    600
gtgctgcagt cctccggcct gtactccctg tcctccgtcg tgaccgtgcc ttcctctagc    660
ctgggcaccc agacctacat ctgcaacgtg aaccacaagc cttccaacac caaggtggac    720
aagaaggtgg agcctaagtc ctgcgacaag acccacacct gtcctccatg ccctgcccct    780
gagctgctgg gcggacccte cgtgttcctg ttccctccaa agcctaagga caccctgatg    840
atctcccgga cccctgaagt gacctgcgtg gtggtggacg tgtcccacga ggatcctgaa    900
gtgaagttca attggtacgt ggacggcgtg gaggtgcaca cgccaagac caagcctcgg    960 gaggaacagt acaactccac ctaccgggtg gtgtccgtgc tgaccgtgct gcaccaggac    1020
tggctgaacg gcaaagagta taagtgcaaa gtctccaaca aggccctgcc tgcccctatc    1080
gaaaagacca tctccaaggc caagggccag cctcgggaac ctcaggtgta caccctgcct    1140
```

```
cccagcaggg acgagctgac caagaaccag gtgtccctga cctgtctggt caagggcttc    1200 taccccttccg atatcgccgt ggagtgggag tctaacggcc agcctgagaa caactacaag   1260 accaccctc ctgtgctgga ctccgacggc tccttcttcc tgtactccaa actgaccgtg     1320
gacaagtccc ggtggcagca gggcaacgtg ttctcctgct ccgtgatgca cgaggccctg    1380
cacaaccact acacccagaa gtccctgtcc ctgtctcctg gcaagtgatg aaagcttggc    1440
gcgcc                                                                1445

<210> SEQ ID NO 18
<211> LENGTH: 1445
<212> TYPE: DNA
<213> ORGANISM: Artificial Sequence
<220> FEATURE:
<223> OTHER INFORMATION: Heavy chain R59E

<400> SEQUENCE: 18
ttaattaagc ttgccaccat ggactggacc tggcggatcc tgtttctggt ggccgctgct     60
accggcacac acgccgaggt gcagctggtg gagtctggcg gaggactggt gcagcctggc   120
ggctccctga gactgtcttg cgccgcctcc ggcttcaaca tcaaggacac ctacatccac   180
tgggtccggc aggctccagg caagggactg gaatgggtgg cccggatcta ccctaccaac   240
ggctacaccg agtacgccga ctccgtgaag ggccggttca ccatctccgc cgacacctcc   300
aagaacaccg cctacctgca gatgaactcc ctgagggccg aggacaccgc cgtgtactac   360
tgctccagat ggggaggcga cggcttctac gccatggact actggggcca gggcaccctg   420
gtcactgtgt cctctgcctc caccaagggc ccttccgtgt ccctctggc cccttccagc     480 aagtctacct ctggcggcac cgctgctctg ggctgcctgg tcaaggacta cttccctgag   540
cctgtgaccg tgtcctggaa ctctggcgcc ctgacctccg gcgtgcacac cttccctgcc   600
gtgctgcagt cctccggcct gtactccctg tcctccgtcg tgaccgtgcc ttcctctagc    660
ctgggcaccc agacctacat ctgcaacgtg aaccacaagc cttccaacac caaggtggac   720
aagaaggtgg agcctaagtc ctgcgacaag acccacacct gtcctccatg ccctgcccct    780
gagctgctgg gcggaccctc cgtgttcctg ttccctccaa agcctaagga caccctgatg   840
atctcccgga cccctgaagt gacctgcgtg gtggtggacg tgtcccacga ggatcctgaa    900
gtgaagttca attggtacgt ggacggcgtg gaggtgcaca cgccaagac caagcctcgg    960 gaggaacagt acaactccac ctaccgggtg gtgtccgtgc tgaccgtgct gcaccaggac    1020
tggctgaacg gcaaagagta taagtgcaaa gtctccaaca aggccctgcc tgcccctatc    1080
gaaaagacca tctccaaggc caagggccag cctcgggaac tcaggtgta caccctgcct   1140 cccagcaggg acgagctgac caagaaccag gtgtccctga cctgtctggt caagggcttc    1200 taccccttccg atatcgccgt ggagtgggag tctaacggcc agcctgagaa caactacaag   1260 accaccctc ctgtgctgga ctccgacggc tccttcttcc tgtactccaa actgaccgtg     1320
gacaagtccc ggtggcagca gggcaacgtg ttctcctgct ccgtgatgca cgaggccctg    1380
cacaaccact acacccagaa gtccctgtcc ctgtctcctg gcaagtgatg aaagcttggc    1440
gcgcc                                                                1445

<210> SEQ ID NO 19
<211> LENGTH: 234
<212> TYPE: PRT
<213> ORGANISM: Artificial Sequence
<220> FEATURE:
```

<223> OTHER INFORMATION: Anti-HER2 light chain

<400> SEQUENCE: 19

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 20
<211> LENGTH: 469
<212> TYPE: PRT
<213> ORGANISM: Artificial Sequence
<220> FEATURE:
<223> OTHER INFORMATION: Anti-HER2 heavy chain

<400> SEQUENCE: 20

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

```
Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 21
<211> LENGTH: 234
<212> TYPE: PRT
<213> ORGANISM: Artificial Sequence
<220> FEATURE:
<223> OTHER INFORMATION: Light chain F53N

<400> SEQUENCE: 21
```

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
50                      55                  60

Lys Leu Leu Ile Tyr Ser Ala Ser Asn Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
130                     135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210                     215                 220

Val Thr Lys Ser Phe Asn Arg Gly Glu Cys
225                 230

<210> SEQ ID NO 22
<211> LENGTH: 234
<212> TYPE: PRT
<213> ORGANISM: Artificial Sequence
<220> FEATURE:
<223> OTHER INFORMATION: Light chain Y92A

<400> SEQUENCE: 22

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
50                      55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Ala
            100                 105                 110

Thr Thr Pro Pro Thr Phe Gly Gln Gly Thr Lys Val Glu Ile Lys Arg
        115                 120                 125

```
Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 23
<211> LENGTH: 234
<212> TYPE: PRT
<213> ORGANISM: Artificial Sequence
<220> FEATURE:
<223> OTHER INFORMATION: Light chain, F53N, Y92A

<400> SEQUENCE: 23

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
50                  55                  60

Lys Leu Leu Ile Tyr Ser Ala Ser Asn Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Ala
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230
```

<210> SEQ ID NO 24

```
<211> LENGTH: 234
<212> TYPE: PRT
<213> ORGANISM: Artificial Sequence
<220> FEATURE:
<223> OTHER INFORMATION: Light chain N30D

<400> SEQUENCE: 24

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asp Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 25
<211> LENGTH: 469
<212> TYPE: PRT
<213> ORGANISM: Artificial Sequence
<220> FEATURE:
<223> OTHER INFORMATION: Heavy chain Y57A

<400> SEQUENCE: 25

Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Ala Thr Arg Tyr Ala
65                  70                  75                  80

Asp Ser Val Lys Gly Arg Phe Thr Ile Ser Ala Asp Thr Ser Lys Asn
```

```
                    85                  90                  95
Thr Ala Tyr Leu Gln Met Asn Ser Leu Arg Ala Glu Asp Thr Ala Val
            100                 105                 110
Tyr Tyr Cys Ser Arg Trp Gly Asp Gly Phe Tyr Ala Met Asp Tyr
            115                 120                 125
Trp Gly Gln Gly Thr Leu Val Thr Val Ser Ser Ala Ser Thr Lys Gly
130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
                180                 185                 190
Pro Ala Val Leu Gln Ser Ser Gly Leu Tyr Ser Leu Ser Ser Val Val
                195                 200                 205
Thr Val Pro Ser Ser Ser Leu Gly Thr Gln Thr Tyr Ile Cys Asn Val
            210                 215                 220
Asn His Lys Pro Ser Asn Thr Lys Val Asp Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
                260                 265                 270
Leu Met Ile Ser Arg Thr Pro Glu Val Thr Cys Val Val Val Asp Val
                275                 280                 285
Ser His Glu Asp Pro Glu Val Lys Phe Asn Trp Tyr Val Asp Gly Val
            290                 295                 300
Glu Val His Asn Ala Lys Thr Lys Pro Arg Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
                340                 345                 350
Pro Ile Glu Lys Thr Ile Ser Lys Ala Lys Gly Gln Pro Arg Glu Pro
                355                 360                 365
Gln Val Tyr Thr Leu Pro Pro Ser Arg Asp Glu Leu Thr Lys Asn Gln
            370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
                420                 425                 430
Thr Val Asp Lys Ser Arg Trp Gln Gln Gly Asn Val Phe Ser Cys Ser
                435                 440                 445
Val Met His Glu Ala Leu His Asn His Tyr Thr Gln Lys Ser Leu Ser
        450                 455                 460
Leu Ser Pro Gly Lys
465

<210> SEQ ID NO 26
<211> LENGTH: 469
<212> TYPE: PRT
<213> ORGANISM: Artificial Sequence
```

<220> FEATURE:
<223> OTHER INFORMATION: Heavy chain R59E

<400> SEQUENCE: 26

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
50                  55                  60

Glu Trp Val Ala Arg Ile Tyr Pro Thr Asn Gly Tyr Thr Glu Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400
```

```
Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly Lys
465
```

1/30

We claim:

1. An antibody or a bivalent fragment thereof that binds preferentially to disease cells having an erbB2 density greater than a normal erbB2 density, the antibody comprising a heavy chain (HC) comprising
   a complementarity determining region (CDR)1 comprising the sequence GFNIKDTYIH (SEQ ID No. 1); a CDR2 comprising the sequence RIYPTNGY$^{57}$TR$^{59}$YADSVKG (SEQ ID No. 2); and a CDR3 comprising the sequence WGGDGFYAMDY (SEQ ID No. 3); and,
   a light chain (LC) comprising
   a CDR1 comprising the sequence RASQDVN$^{30}$TAVA (SEQ ID No. 4); a CDR2 comprising the sequence SASF$^{53}$LYS (SEQ ID No. 5); and a CDR3 comprising the sequence QQHY$^{92}$TTPPT (SEQ ID No. 6), wherein the light chain contains substitutions consisting of LC F53N and LC Y92A.

2. An antibody or a bivalent fragment thereof that binds preferentially to disease cells having an erbB2 density greater than a normal erbB2 density, the antibody comprising a heavy chain (HC) comprising
   a complementarity determining region (CDR)1 comprising the sequence GFNIKDTYIH (SEQ ID No. 1); a CDR2 comprising the sequence RIYPTNGY$^{57}$TR$^{59}$YADSVKG (SEQ ID No. 2); and a CDR3 comprising the sequence WGGDGFYAMDY (SEQ ID No. 3); and,
   a light chain (LC) comprising
   a CDR1 comprising the sequence RASQDVN$^{30}$TAVA (SEQ ID No. 4); a CDR2 comprising the sequence SASF$^{53}$LYS (SEQ ID No. 5); and a CDR3 comprising the sequence QQHY$^{92}$TTPPT (SEQ ID No. 6), wherein the light chain and heavy chain contain substitutions consisting of HC Y57A and LC N300.

3. An antibody according to claim 1, the antibody having the framework region sequences of trastuzumab.

4. An antibody according to claim 1, the antibody having the framework region sequences and the constant region sequence of trastuzumab.

5. A bivalent fragment of an antibody according to claim 1.

6. A conjugate comprising a cytotoxin or a detectable label and, conjugated thereto, an antibody or bivalent fragment thereof as defined according to claim 1.

7. A pharmaceutical composition comprising a pharmaceutically acceptable carrier and an antibody in an amount useful to control the growth of cells presenting erbB2 at a density greater than the normal erbB2 density, in a subject in need thereof, wherein the antibody is an antibody or bivalent fragment thereof as defined according to claim 1.

8. An antibody according to claim 2, the antibody having the framework region sequences of trastuzumab.

9. An antibody according to claim 2, the antibody having the framework region sequences and the constant region sequence of trastuzumab.

10. A bivalent fragment of an antibody according to claim 2.

11. A conjugate comprising a cytotoxin or a detectable label and, conjugated thereto, an antibody or bivalent fragment thereof as defined according to claim 2.

12. A pharmaceutical composition comprising a pharmaceutically acceptable carrier and an antibody in an amount useful to control the growth of cells presenting erbB2 at a density greater than the normal erbB2 density, in a subject in need thereof, wherein the antibody is an antibody or bivalent fragment thereof as defined according to claim 2.

* * * * *